United States Patent [19]

Kato et al.

[11] Patent Number: 5,077,803
[45] Date of Patent: Dec. 31, 1991

[54] BIOLOGICAL DETECTING SYSTEM AND FINGERPRINT COLLATING SYSTEM EMPLOYING SAME

[75] Inventors: Masayuki Kato; Takashi Shinzaki, both of Atsugi; Seigo Igaki, Inagi; Fumio Yamagishi, Ebina; Hiroyuki Ikeda, Yokohama, all of Japan

[73] Assignee: Fujitsu Limited, Kawasaki, Japan

[21] Appl. No.: 408,090

[22] Filed: Sep. 14, 1989

[30] Foreign Application Priority Data

Sep. 16, 1988 [JP] Japan .................................. 63-230052
Nov. 15, 1988 [JP] Japan .................................. 63-286792
Nov. 25, 1988 [JP] Japan .................................. 63-298921

[51] Int. Cl.⁵ .................................................. G06K 9/00
[52] U.S. Cl. .......................................... 382/4; 356/71
[58] Field of Search .......................... 382/4, 5; 356/71

[56] References Cited

U.S. PATENT DOCUMENTS 4,553,837 11/1985 Marcus ................................ 356/71
4,783,167 11/1988 Schiller et al. ......................... 382/4
4,936,680 6/1990 Henkes et al. .......................... 382/4

FOREIGN PATENT DOCUMENTS 0045915  2/1982  European Pat. Off. .
0098607  1/1984  European Pat. Off. .
0190628  8/1986  European Pat. Off. .
0194783  9/1986  European Pat. Off. .
61-221883 10/1986 Japan .
62-74173  4/1987  Japan .
3635386  4/1987  Netherlands .

Primary Examiner—Leo H. Boudreau
Attorney, Agent, or Firm—Staas & Halsey

[57] ABSTRACT

A biological detecting system comprising a light source; a condensing optical system for condensing a light beam from the light source and irradiating the surface of a sample to be detected with a spot of light, an imaging optical system for condensing light reflected or scattered by an irradiated portion of the sample and forming an image of the irradiated portion at a predetermined location, and a photodetector arranged at the predetermined location to detect the size of the image of the irradiated portion and output a detection signal indicating the detected size of the image.

30 Claims, 22 Drawing Sheets

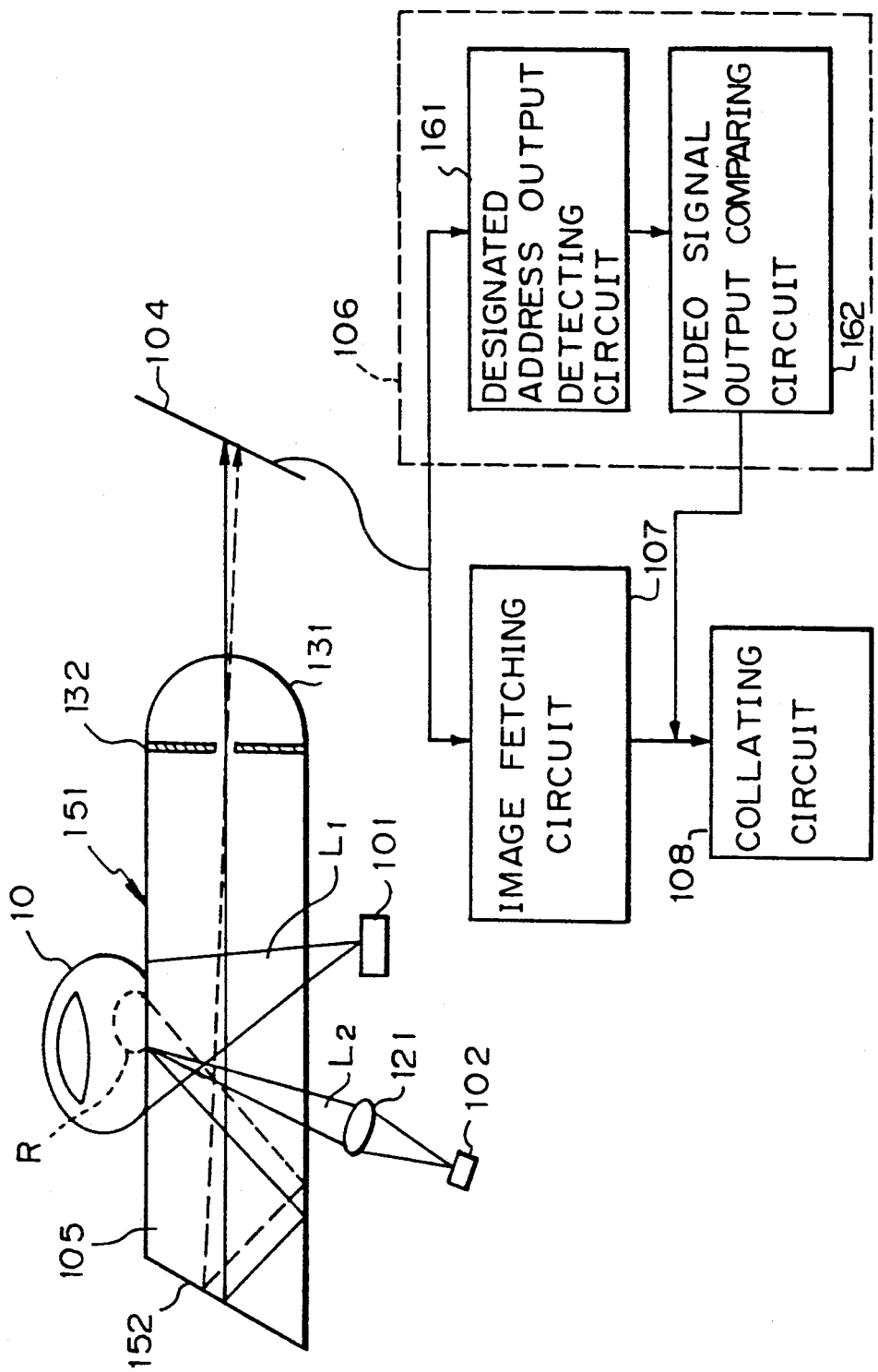

Fig. 31
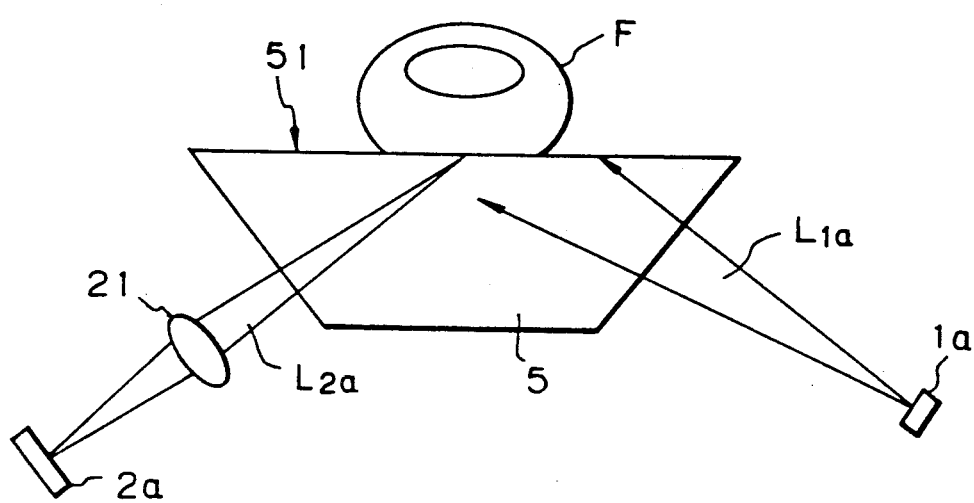
Fig. 32 [PRIOR ART]
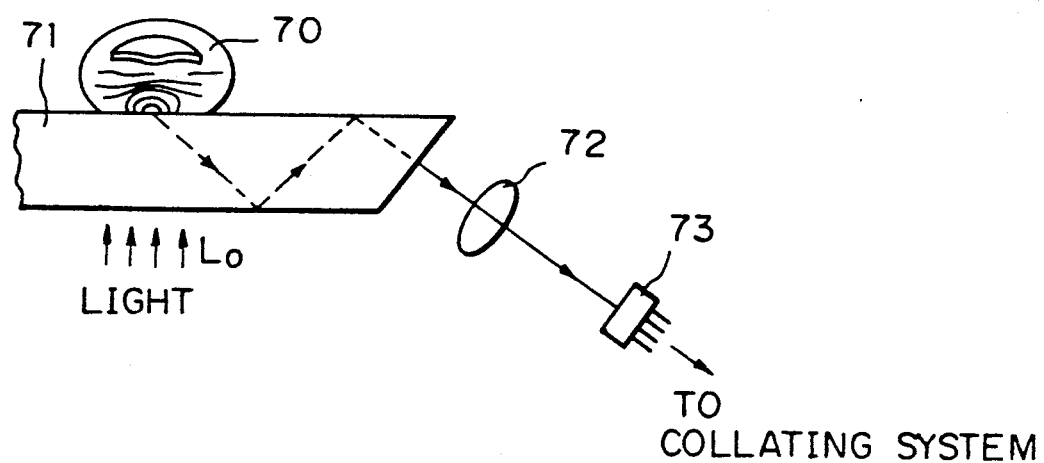

Fig. 33 [PRIOR ART]
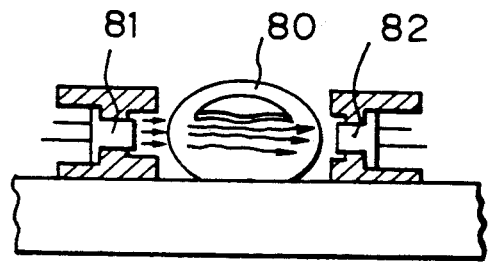
Fig. 34 [PRIOR ART]
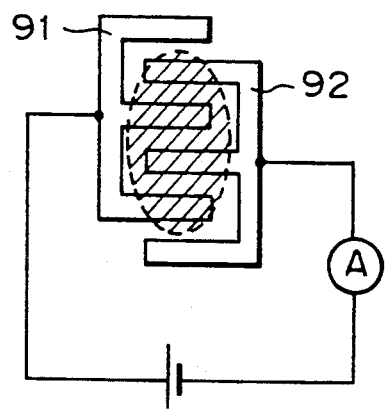
Fig. 35 [PRIOR ART]
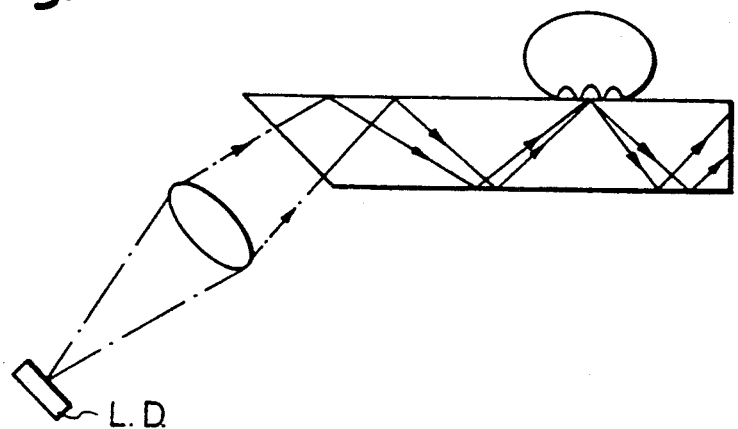

BIOLOGICAL DETECTING SYSTEM AND FINGERPRINT COLLATING SYSTEM EMPLOYING SAME

CROSS-REFERENCE TO RELATED APPLICATIONS

U.S. patent application Ser. No. 07/370,768 of Masayuki KATO et al. entitled "UNEVEN-SURFACE DATA DETECTION APPARATUS" filed June 23, 1989, assigned to the common assignee of the present application, Fujitsu Limited, as shown by the assignment records of the United States Patent and Trademark Office, is related to the invention of the present, new U.S. patent application.

BACKGROUND OF THE INVENTION

1. Field of the Invention

The present invention relates to a biological detecting system and a fingerprint collating system employing that biological detecting system.

2. Description of the Related Art

The increasing growth and use of information systems has raised a problem of how to maintain the security of such systems. Currently, as one means of identifying a person allowed to use the information system, an ID card is employed, but the ID card is easily lost or stolen. Also, it is relatively simple to obtain a code number of the ID card using known information about the owner of the card. Accordingly, as a substitute for the ID card, use is made of fingerprints, since these are different for each person and do not change during a person's life time, and therefore, various simple individual collating apparatuses for fingerprints and fingerprint collating system have been developed. In the fingerprint collating systems, a fingerprint is handled as an image, and therefore, in this kind of system an input apparatus must be provided for converting a detected image of the fingerprint into image data.

FIG. 32 is a schematic view of a typical arrangement of a fingerprint image input apparatus. In the operation of this apparatus, a finger 70 is placed in contact with a transparent member 71, and the finger is illuminated as indicated by the arrows. Among light scattered from ridges (projecting portions) of a fingerprint, components (indicated by dotted lines) thereof that are totally reflected by interfaces of the transparent member are collected by an optical system 72 to form an image, and a photodetector 73 such as a charge-coupled-device (CCD) is used to obtain an image of the ridge pattern.

Nevertheless, a replica having the same irregular pattern as the pattern of a previously registered fingerprint can be produced, and can be used for the fingerprint collation, and thus the system security is not foolproof. Accordingly, there is a need for a mechanism capable of judging whether the irregular pattern of a sample in contact with the fingerprint image input apparatus originates from a genuine finger (a biological object) or from a replica (a non-biological object), i.e., a biological detecting mechanism is required.

An example of a conventional biological detecting system is shown in FIG. 33. This first prior art example is an optical system utilizing a phenomenon that an amount of light transmitted through a human body will be changed by a pulsation of the human body. Namely, the transparency to light of a finger 80 under a red light from a light source 81 is changed in the same cycle as that of the pulsation of the human body, and this cycle of change of the transparency is detected by a photodetector 82 to determine whether or not the sample is a biological object.

Another system (second prior art example) is shown in FIG. 34. This is an electrical system utilizing a difference between the resistance value of a finger and the resistance value of a replica. On a surface (a hatched portion), with which contact is made by a finger, are arranged transparent electrodes 91 and 92 for measuring a resistance value of the finger and the measured value is compared with a preset resistance value of a replica to determine whether or not the finger is a biological object. In this case, a fingerprint image input apparatus receives an image of the fingerprint to be compared and judged, together with images of the electrode patterns.

According to the first prior art example, a time of several seconds or more is needed to detect the pulsation, and therefore, to perform a biological detection, the finger must be kept in contact with the fingerprint image input apparatus for the time necessary to detect the pulsation. This is disadvantageous in that, if the contact by a sample is broken before that time has elapsed, it is impossible to determine whether or not the sample is a biological object.

The second prior art requires only a short time for carrying out the biological detection, but the electrode patterns may disturb an image of the fingerprint. Therefore, although the biological detection can be carried out without hindrance, it may be difficult to carry out the fingerprint collation after the biological detection is effected. Further, the resistance value of a human finger may vary in accordance with the pressure applied and the presence of perspiration on the skin. To cope with this problem, the allowable resistance value must be very large, but if the allowable resistance value is large, a difference between a reference value and the resistance value of the replica becomes smaller, and thus it becomes difficult to carry out the comparison and determination in the biological detection. Also, it would be possible to provide a replica with the same resistance value as a human finger, and thus the security of system will be compromised.

SUMMARY OF THE INVENTION

Therefore, to solve the above problems of the prior art, an object of the invention is to provide a biological detecting system that cannot be influenced by the conditions of a sample and can instantaneously determine whether or not the sample is a biological object.

Another object of the invention is to provide a system for collating a fingerprint by employing such a biological detecting system.

The present invention is based on the phenomenon that, when the surface of a sample is irradiated with a spot of light, the condition of the illumination of the surface is peculiar to that sample. Namely, if the sample is a biological object (a finger), not only does illumination occur at the irradiated portion of the finger illumination due to reflection but also at the periphery of the irradiated portion, the latter occurring because the irradiated light is propagated and diffused inside the finger and is reflected and scattered in the finger. On the other hand, if the sample is not a biological object (for example, if the sample is a replica made of silicon (Si) based rubber), illumination occurs at only a part very close to the irradiated portion, due to reflection and scatter.

Therefore, if an irradiated point of a sample is set as an object point of an imaging optical system, the size of the object point varies in accordance with whether or not the sample is a biological object. Also, the size of an image of the sample to be formed varies in accordance with whether or not the sample is a biological object. Therefore, by detecting the size of the image and comparing it with a reference value, it is possible to determine whether or not the sample is a biological object.

Therefore, according to a first aspect of the present invention there is provided a biological detecting system which comprises, a light source; a condensing optical system for condensing a light beam $L_1$ from the light source and irradiating the surface of a sample with a spot of light; an imaging optical system for condensing light reflected and scattered by an irradiated portion of the sample and forming an image of the irradiated portion on a predetermined location; and photodetector means arranged at the predetermined location to detect the size of the image of the irradiated portion and output a detection signal indicating the detected size of the image.

According to a second aspect of the invention, there is provided a biological detecting system comprising a light source; a condensing optical system for condensing a light beam from the light source and irradiating the surface of a sample with a spot of light; an imaging optical system for condensing light reflected and scattered by an irradiated portion of the sample and forming an image of the irradiated portion on a predetermined location; and photodetector means arranged at the predetermined location to detect the size of the image of the irradiated portion and to detect whether or not the center of a region of the sample at which the irradiating light beam is reflected and scattered is displaced from the center of the irradiated portion, and to output a detection signal $J_2$ indicating the size of the image and the presence or absence of displacement.

If the scattering light is polarized in a predetermined direction, the light intensity of a component in the polarization direction will vary in accordance with whether the sample is a biological object (a finger) or a non-biological object (a replica). Therefore, by comparing and discriminating polarization states based on the light intensity of components in the polarization direction, it is possible to determine whether or not the sample is a biological object.

According to a third aspect of the invention, there is provided a biological detecting system comprising a light source; a polarizing and condensing optical system for linearly polarizing and condensing a light beam from the light source to irradiate the surface of a sample with a spot of light; a condensing and polarizing optical system for condensing light reflected and scattered by an irradiated portion of the sample, and polarizing the condensed light in a predetermined direction; and photodetector means for detecting the intensity of a polarized component of the polarized light and outputting a detection signal $J_3$ indicating a polarization state based on the detected light intensity of the polarized light. A determination of whether or not the sample is a biological object is made in accordance with the detection signal output from the photodetector means.

The present invention also provides a fingerprint collating system comprising a biological detecting system based on any one of the first to third aspects. Here, only when a sample is a finger does the fingerprint collating system convert a pattern of the finger into image data and compare the converted image data with previously registered image data of a fingerprint, to identify the sample.

The first and second aspects mentioned in the above utilize a phenomenon whereby, when the surface of a sample is irradiated with a spot of light, the illumination of the surface is peculiar to that sample. Based on this concept, the size of an image of the sample is detected, or it is determined whether or not the center of a region of the sample, where reflection and scattering occur, is displaced from the center of an irradiated portion of the sample, and thus it is determined whether the sample is a biological object (a genuine finger) or a non-biological object (a replica). The third aspect utilizes a phenomenon whereby, when the surface of a sample is irradiated with linearly polarized light, polarization characteristics of light reflected and scattered by the surface are essentially different, depending on whether the sample is a human finger or a replica. Namely, based on the light intensity of polarization directional components, polarization states are compared with a reference value to determine whether or not the sample is a biological object.

As described above, the biological detecting system of the invention can instantaneously determine whether or not a sample is a biological object, without being influenced by conditions of the sample (such as perspiration, pressure applied, and a time for which the sample is in contact with a detecting system).

BRIEF DESCRIPTION OF THE DRAWINGS

The above and other features and operations of the embodiments of the present invention will be explained in detail with reference to the accompanying drawings, in which:

FIGS. 4A to 4C are views showing an embodiment according to the first aspect shown in FIG. 1, wherein FIG. 4A is a top view, FIG. 4B a view taken along an arrow B in FIG. 4A and FIG. 4C a view taken along an arrow C in FIG. 4A;

FIG. 26 is a block diagram of a fingerprint image input apparatus shown in FIGS. 25A and 25B;

FIG. 31 is an enlarged view of a part of FIG. 30;

FIG. 32 is a side schematic view of the arrangement of a typical fingerprint image input apparatus;

FIG. 33 is a view explaining a biological detecting system according to the prior art;

FIG. 34 is a view explaining a biological detecting system according to another prior art; and FIG. 35 is a view explaining problems of the prior art.

DESCRIPTION OF THE PREFERRED EMBODIMENTS

Figure 1:
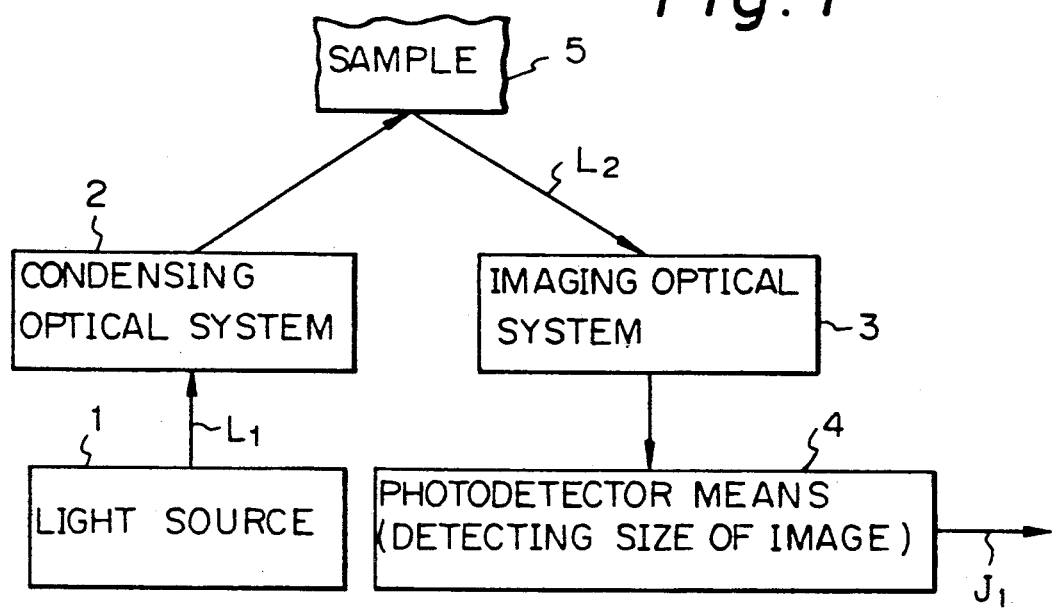
FIG. 1 is a view showing the principle of a biological detecting system according to a first aspect of the present invention.

FIG. 1 shows the principle of operation of a biological detecting system according to the first aspect of the present invention, which comprises a light source 1 and a condensing optical system 2 for condensing a light beam $L_1$ from the light source and irradiating the surface of a sample 5 to be detected with a spot of light. The detecting system also comprises an imaging optical system 3 for condensing the light beam $L_2$ reflected and scattered by an irradiated portion of the sample 5 and forming an image of the irradiated portion at a predetermined location and photodetector means 4 arranged at the predetermined location to detect the size of the image of the irradiated portion and output a detection signal $J_1$ indicating the detected size of the image. A determination of whether or not the sample is a biological object is made in accordance with the detection signal output from the photodetector means.

When the surface of a sample 5 is obliquely irradiated with a spot of light, and if the sample 5 is a genuine finger, the irradiated light is diffused inside the finger so that the center of a region of the finger from which the irradiated light is reflected and scattered is displaced from the center of the direction irradiated portion of the finger. Conversely, if the sample is a replica, the irradiated light is not propagated and diffused inside the replica, and thus the displacement does not occur.

Therefore, by detecting the size of an image of the sample and the presence or absence of displacement, it can be determined whether or not the sample is a biological object.

Figure 2:
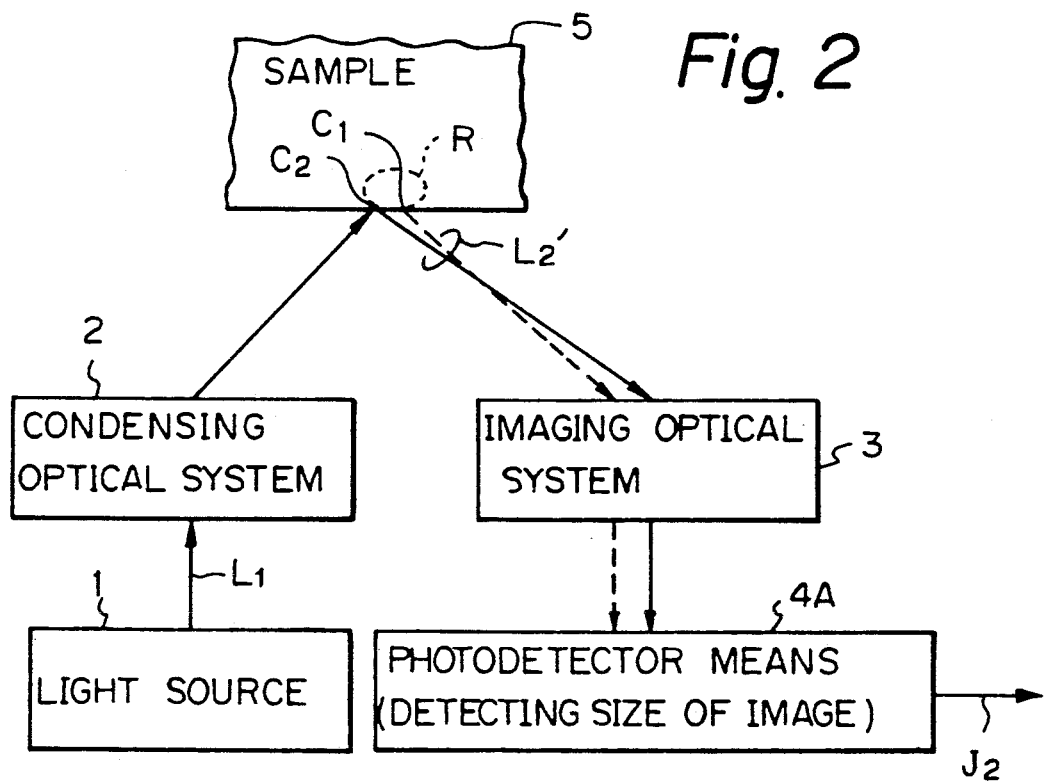
FIG. 2 is a view showing the principle of a biological detecting system according to a second aspect of the present invention.

Accordingly, the second aspect of the present invention, as shown in FIG. 2, provides a biological detecting system comprising a light source 1, a condensing optical system 2 for condensing a light beam $L_1$ from the light source and irradiating the surface of a sample 5 to be detected with a spot of light, an imaging optical system 3 for condensing the light beam $L_2$ reflected and scattered by an irradiated portion of the sample 5 and forming an image of the irradiated portion on a predetermined location, and photodetector means 4A arranged at the predetermined location to detect the size of the image of the irradiated portion and to determine whether or not the center $C_1$ of a region R of the sample from which the irradiated light beam is reflected and scattered is displaced from the center $C_2$ of the directly irradiated portion, and output a detection signal $J_2$ indicating the size of the image and the presence or absence of displacement. A determination of whether or not the sample is a biological object is made in accordance with the detection signal output from the photodetector means.

In addition, when a spot of light is linearly polarized to irradiate the surface of a sample, the irradiated light is reflected by the sample, and if the sample is a finger, the irradiated light is also reflected and scattered inside the finger to provide scattered light having components with various polarization directions.

Figure 3:
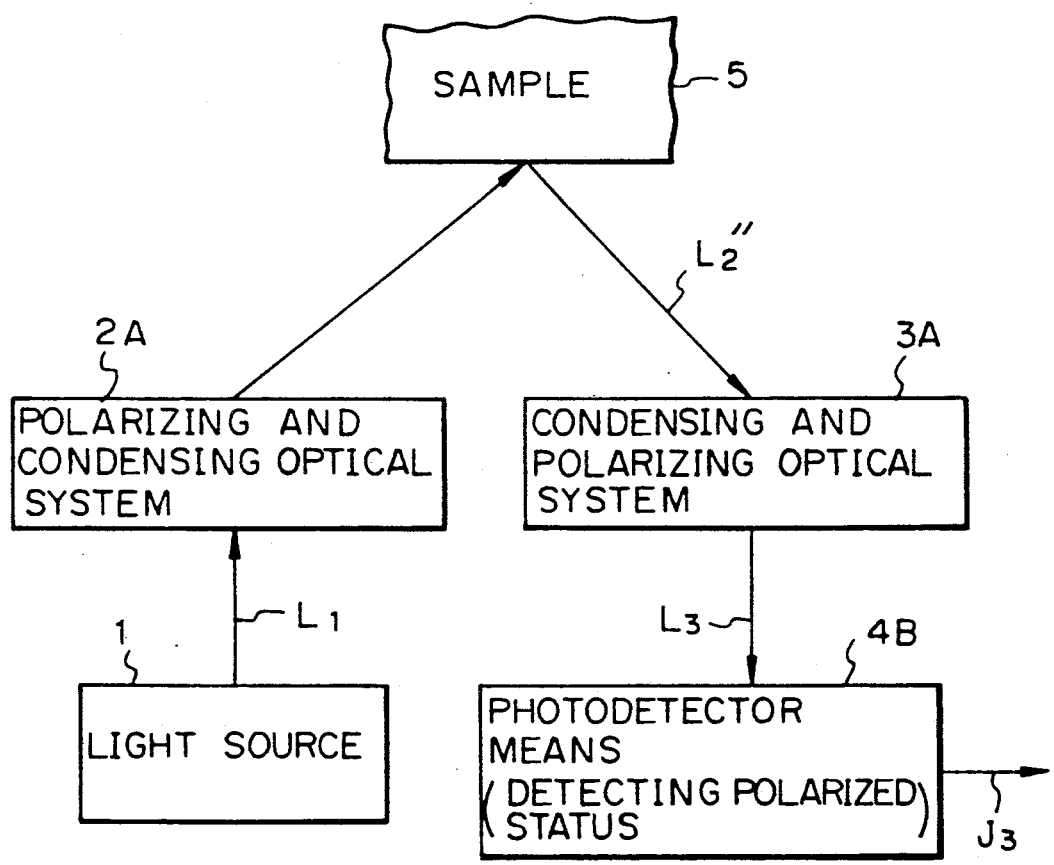
FIG. 3 is a view showing the principle of a biological detecting system according to a third aspect of the present invention.

A biological detecting system according to a third aspect of the present invention, as shown in FIG. 3, comprises a light source 1; a polarizing and condensing optical system 2A for linearly polarizing and condensing a light beam $L_1$ from the light source 1 to irradiate the surface of a sample 5 to be detected with a spot of light; a condensing and polarizing optical system 3A for condensing light $L_2$ reflected and scattered by an irradiated portion of the sample and polarizing the condensed light in a predetermined direction; and a photodetector means 4B for detecting the intensity of a polarized component of the polarized light $L_3$ and outputting a detection signal $J_3$ indicating a polarization state based on the detected light intensity of the polarized light. A determination of whether or not the sample is a biological object is made in accordance with the detection signal output from the photodetector means.

Figure 4A:
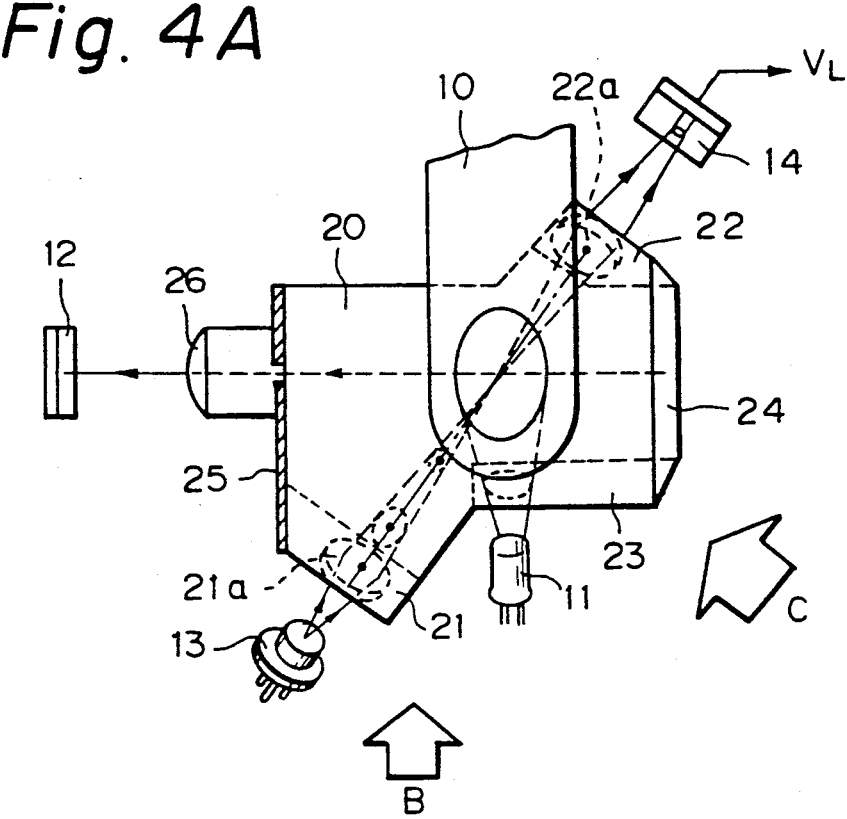
Figure 4B:
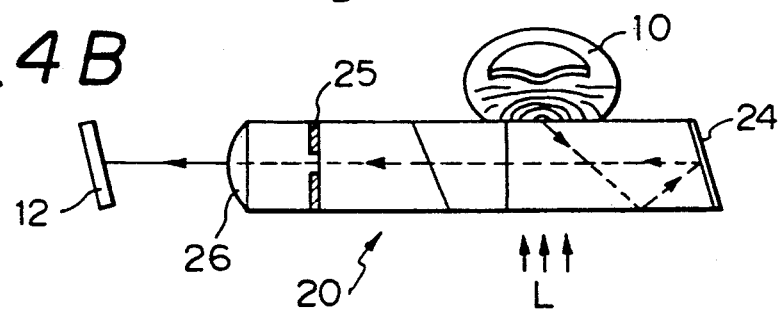
Figure 4C:
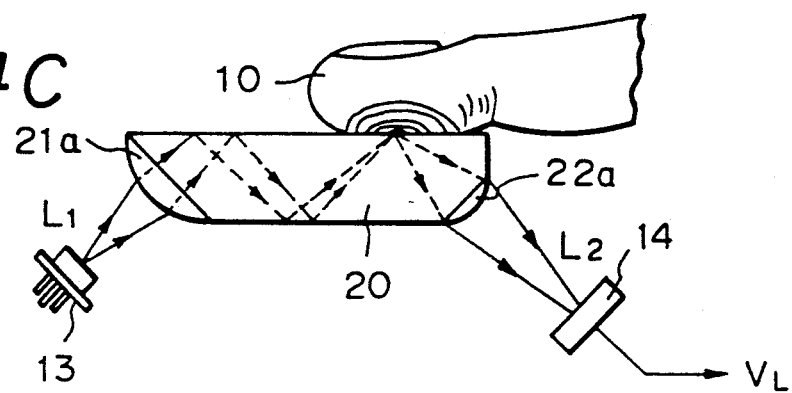

FIGS. 4A and 4B show an embodiment according to the first aspect (FIG. 1) of the present invention, wherein FIG. 4A is a top view, FIG. 4B is a side view taken along an arrow B in FIG. 4A to show an imaging optical system for forming the image of a fingerprint, and FIG. 4C is a side view taken along an arrow C in FIG. 4A to show an optical system for detecting a biological object according to the present invention. The system shown in FIGS. 4A–4C constitutes part of a fingerprint image input apparatus of a fingerprint collating system.

In FIGS. 4A–4C, 10 represents a finger (a genuine finger or a replica made of silicon based rubber) as a sample; 11 a light emitting diode (LED) employed as a finger irradiating light source used to form an image of the fingerprint; 12 a charge-coupled-device (CCD) employed as a fingerprint image detecting element for generating an electric signal indicating the image of a fingerprint in response to light corresponding to the image of the fingerprint; 13 a semiconductor laser (or LED) employed as a light source for detecting a biological object; and 14 a photodetector having a light receiving area divided into a plurality of regions. The output of the photodetector 14 is represented by $V_L$.

Further, 20 denotes a transparent light guiding board having four diagonal cut faces 21 to 24, cut diagonally in a cross-sectional direction. A lens 21a is adhered to the diagonal cut face 21 to focus a light beam from the semiconductor laser 13, and a lens 22a is adhered to the diagonal cut face 22 to focus a light beam emitted from the light guiding board 20 onto a light receiving face of the photodetector 14. The diagonal cut faces 21 and 22 are cut on opposite sides of the light guiding board 20 such that a light beam focused by the lens 21a is totally and repeatedly reflected in the light guiding board 20, reflected and scattered by the portion of the light guiding board 20 with which the finger 10 is in contact, and then passed through the lens 22a to finally reach the light receiving face of the photodetector 14. The diagonal cut face 24 forms a mirror face, and an opening diaphragm portion 25 is formed on one side face of the light guiding board 20 facing (i.e., oppositely disposed from) the diagonal cut face 24. A lens 26 is adhered to the opening diaphragm portion 25 to focus a light beam emitted from the light guiding board 20 onto a light receiving face of the CCD 12, and in this case, the diagonal cut face 24 is shaped such that a light beam emitted from the light source (LED) 11 and reflected and scattered by the finger 10 is totally reflected by the bottom face of the light guiding board 20 and reflected by the diagonal cut face 24 which thus functions as a mirror, thereby to be incident on the light receiving face of the CCD 12 through the opening of the opening diaphragm portion 25 and the lens 26.

Figure 5:
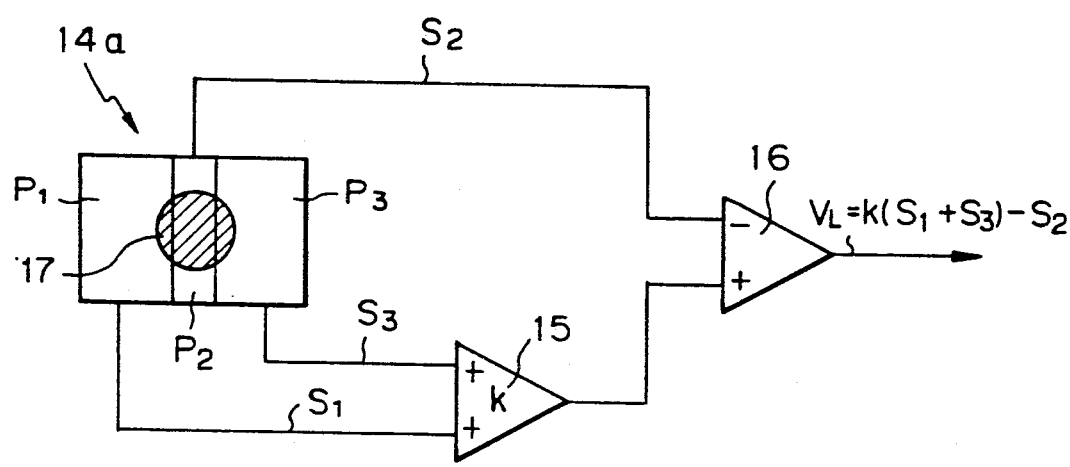
FIG. 5 is a circuit diagram showing a typical example of the arrangement of a photodetector of FIG. 4.

FIG. 5 shows an example of the photodetector shown in FIG. 4.

The photodetector 14 comprises a light receiving element having a light receiving face 14a divided into three light receiving regions $P_1$, $P_2$, and $P_3$; an operational amplifier 15 having a gain of k (constant) for determining the total value of optical outputs $S_1$ and $S_3$ corresponding to the respective amounts of light received by the light receiving side regions $P_1$ and $P_3$; and an operational amplifier 16 for determining the difference between the output of the operational amplifier 15 and an optical output $S_2$ corresponding to the amount of light received by the light receiving central region $P_2$. The constant k is a coefficient for correcting for the difference between $(S_1+S_3)$ and $S_2$. Therefore, an output $V_L$ of the photodetector 14 is expressed as "k $(S_1+S_3)-S_2$".

In the figure, a hatched portion 17 indicates an image of the finger 10, which image is obtained by a light beam emitted from the semiconductor laser 13. The light beam is irradiated on the finger 10 and is reflected and scattered by the finger 10 to form the image on the light receiving face 14a of the photodetector.

The operation (biological detection) of the embodiment of FIG. 4 will be explained with reference to FIGS. 6A to 6F.

Figure 6A:
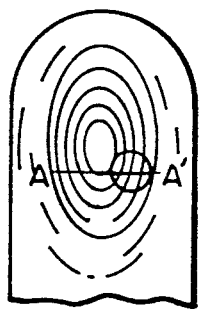
FIGS. 6A to 6F are views explaining the principle of the biological detection used in the embodiment of FIGS. 4A to 4C.
Figure 6B:
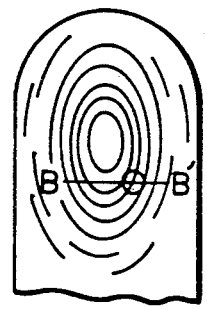
Figure 6C:
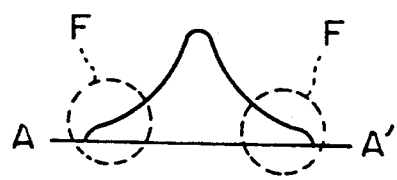
Figure 6D:
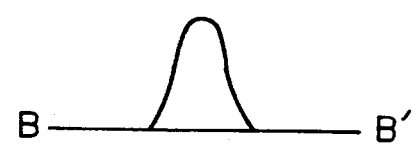
Figure 6E:
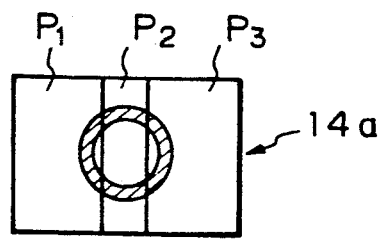
Figure 6F:
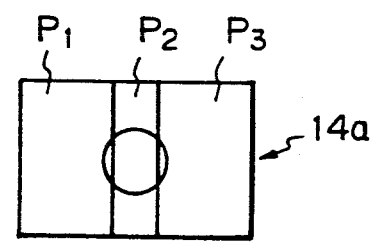

FIG. 6A shows a typical fingerprint of a genuine finger, FIG. 6B shows a typical fingerprint of a replica, FIG. 6C is a light intensity distribution diagram taken along a line A—A' of an irradiated portion of FIG. 6A, FIG. 6D is a light intensity distribution diagram taken along a line B—B' of an irradiated portion of FIG. 6B, FIG. 6E shows a typical image appearing on the light receiving face 14a of the photodetector of FIG. 6A, and FIG. 6F shows a typical image appearing on the light receiving face 14a of the photodetector of FIG. 6B.

If the finger 10 is genuine, illumination occurs not only at the directly irradiated portion of the finger due to reflection, but also at the periphery of the irradiated portion, because the irradiated light is propagated and diffused inside the finger and is reflected and scattered in the finger, as described before. Namely, as indicated by a broken line F in FIG. 6C, a flared area of illumination occurs, and as a result, portions of the image appearing on the light receiving face 14a of the photodetector that extend over the light receiving side-regions $P_1$ and $P_3$ as indicated by a hatched portion in FIG. 6E, will increase, and accordingly, the photodetector 14 will provides an output $V_L$ that tends toward a positive (+) value (FIG. 5).

If the finger 10 is a replica, however, illumination will occur at only a portion thereat quite close to the irradiated portion, due to reflection and scattering; i.e., flare does not occur, and as a result an incidence ratio on the light receiving region $P_2$ of an image appearing on the light receiving face 14a of the photodetector will increase, as shown in FIG. 6F, and therefore an output $V_L$ of the photodetector 14 is reduced and moved toward a negative (−) value.

Figure 7:
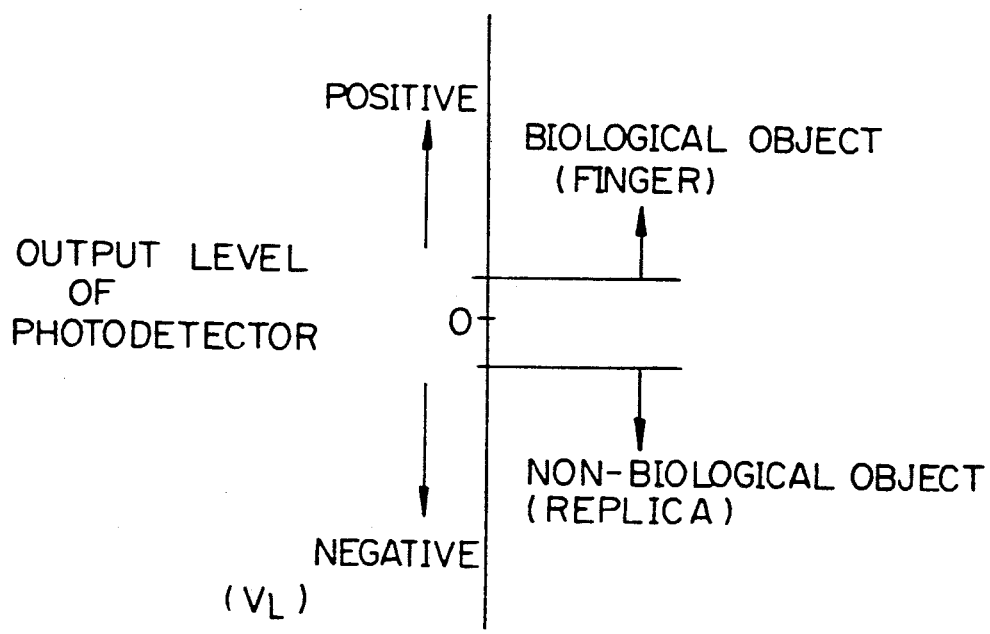
FIG. 7 is a view showing the relationship between an output level of the photodetector of FIG. 5 and the determination levels of biological and nonbiological objects.

In this embodiment, a gap between the photodetector 14 and the light guiding board 20, the positional relationships of the respective components, and the sizes of the respective light receiving regions $P_1$, $P_2$, and $P_3$ of the photodetector 14 are set such that the output $V_L$ of the photodetector 14 will be positive when the sample is a genuine finger but will be negative when the sample is a replica (FIG. 7).

As described above, the embodiment of FIG. 4 can instantaneously determine, based on the positive or negative state of the signal $V_L$ output from the photodetector 14, whether the finger 10 is a genuine finger (a biological object) or a replica (a non-biological object).

According to the embodiment of FIG. 4, light is obliquely irradiated on a contacting face of the finger, and light obliquely reflected by the finger is detected, but a half mirror, for example, may be employed instead to make light incident from just below the contacting face of the finger and detect light reflected by the finger toward just below the finger.

Figure 8:
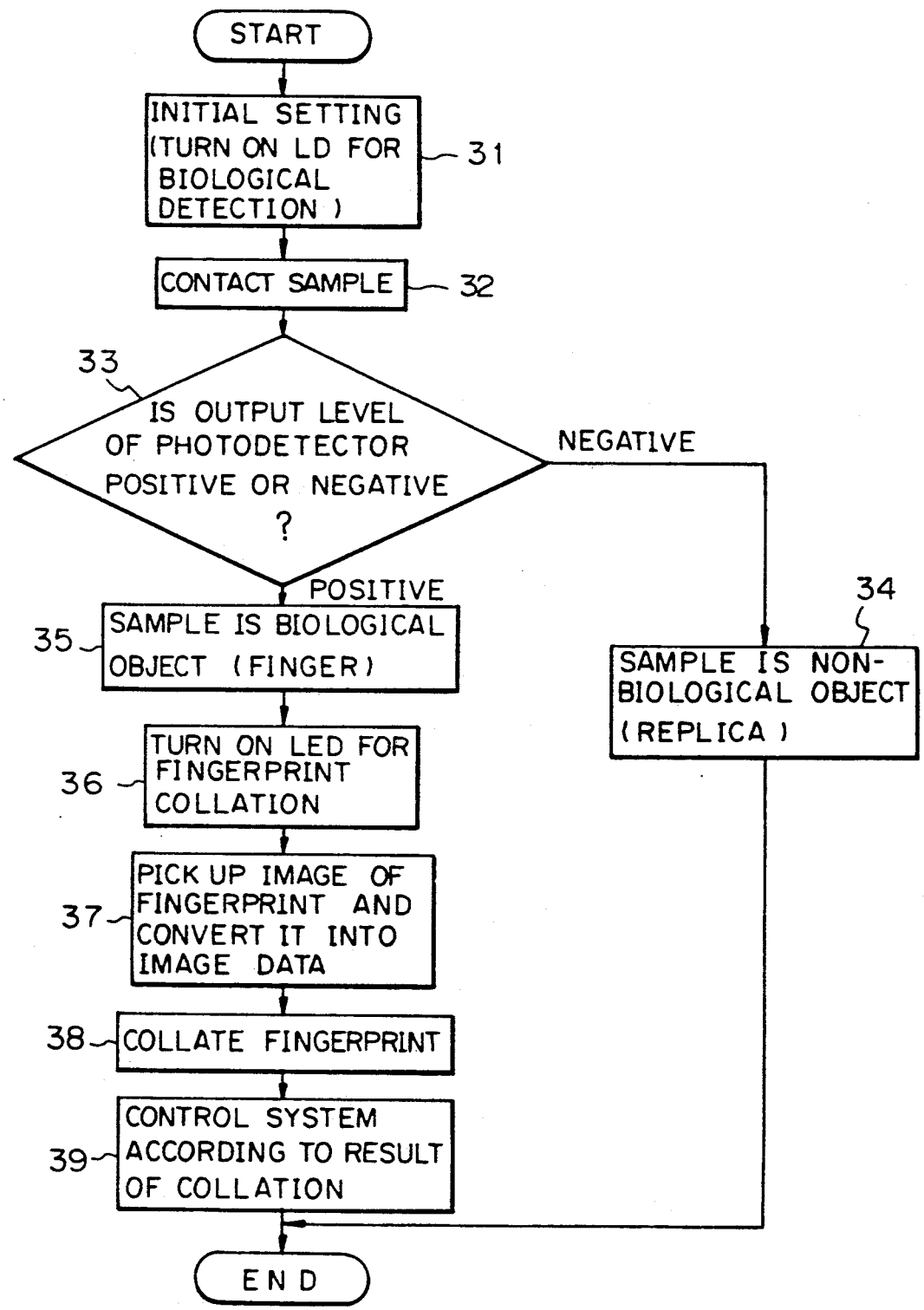
FIG. 8 is a flowchart showing the process of the biological detecting and fingerprint collating operations in a fingerprint collating system to which the embodiment shown in FIGS. 4A to 4C is applied.

The biological detecting system explained above can be assembled in a fingerprint image input apparatus of a fingerprint collating system. The operation processes of the biological detection and fingerprint collation in a fingerprint collating system employing the embodiment shown in FIG. 4 will be explained with reference to FIG. 8.

First, in step 31, an initial setting is made, i.e., the semiconductor laser (LD) 13 for detecting a biological object is turned ON. Then, the semiconductor laser 13 emits a light beam which passes through the lens 21a and is made incident on the light guiding board 20. This light beam is totally and repeatedly reflected, passed through the lens 22a, and focused on the light receiving face 14a of the photodetector 14. A light path shown in FIG. 4(A) extending from the semiconductor laser 13 to the photodetector 14 is only an example, and it will be apparent to a person skilled in the art that many light paths other than the abovementioned light path can be adopted.

In step 32, the sample, i.e., the finger 10, is positioned at a predetermined point on the light guiding board 20, and in step 33, it is determined whether the output level $V_L$ of the photodetector is positive or negative, by a fingerprint collating apparatus (not shown) that determines the output level $V_L$ of the photodetector 14. If the output level $V_L$ of the photodetector is negative, it is determined in step 34 that the sample is a non-biological object (a replica) and the following fingerprint collation processes are not executed. Namely, the process flow is terminated (END).

If the output level $V_L$ of the photodetector is positive, at step 35 the fingerprint collating system determines that the sample is a biological object (a genuine finger) and outputs a control signal indicating that determination to a fingerprint image input apparatus (the biological detecting apparatus). The biological detecting apparatus receives the control signal, and in step 36 turns ON the fingerprint collating LED 11, and the light beam emitted from the LED 11 is passed through the orthogonal cut face 23 and made incident on the light beam guiding board 20. This light is reflected by the contacting face of the finger and totally reflected by the bottom face of the light guiding board 20, as indicated by a broken line of FIG. 4B, and then the light beam is reflected by the mirror face 24 and propagated in the light beam guiding board 20. The light is then passed through the opening of the opening diaphragm portion 25 and the lens 26 and focused on the light receiving face of the CCD 12. In FIG. 4A, a light path from the LED 11 to the CCD 12 is only an example, and light paths other than this light path can be used.

In step 37, the fingerprint image input apparatus picks up a fingerprint image formed on the CCD 12 and converts that fingerprint image into image data, and in step 38, the fingerprint collating apparatus compares the image data with previously registered image data of a fingerprint, to identify the fingerprint. Then in the final step 39, the system is controlled according to a result of the fingerprint collation. For example, in a system for controlling the entry of personnel into a computer room, if the fingerprint of a person is found to be not authentic, the system prohibits the entry of that person to the computer room.

If the fingerprint collating LED 11 is turned ON in step 36, this may cause noise affecting the biological detecting system. Therefore, the light emission for the biological detection and the light emission for fingerprint collation are preferably carried out in time series, but the biological detection (steps 31 to 33 and 35), fingerprint illumination (step 36), and fingerprint image picking up (step 37) must be carried out within a short time of, for example, several 10 ms. This will prevent an illegal action such as replacement of a finger with a replica after completion of the biological detection.

Figure 9:
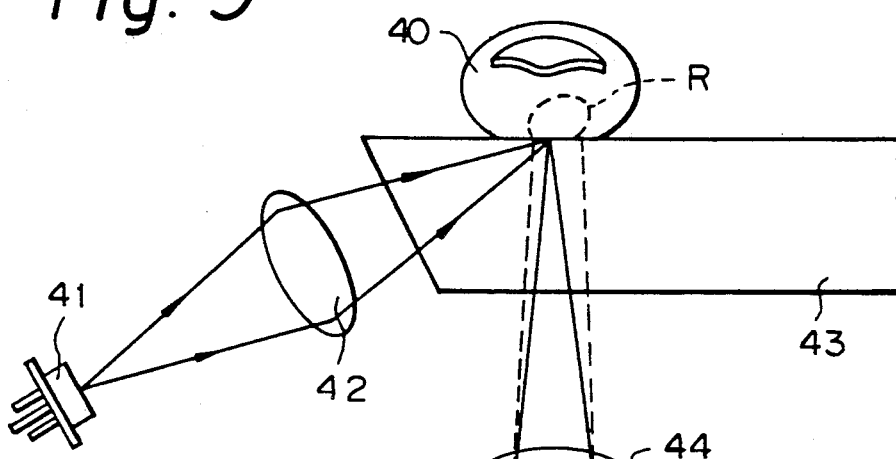
FIG. 9 is a view showing an embodiment according to the second aspect of the present invention shown in FIG. 2.

FIG. 9 shows an embodiment according to the second aspect (FIG. 2) of the present invention.

In FIG. 9, 40 denotes a finger (a genuine finger or a replica) as a sample; 41 a semiconductor laser (or LED) as a light source for detecting a biological object; 42 a condensing optical system (a lens) for condensing a light beam from the light source 41 and irradiating the surface of the finger 40 with a spot of light; 44 an imaging optical system (a lens) for condensing the light beam reflected and scattered by the surface of the finger and forming an image of an irradiated portion of the finger at a predetermined location; 45a and 45b photodetectors disposed at predetermined positions; and 46 a comparator circuit. The comparator circuit 46 responds to optical outputs Sa and Sb corresponding to amounts of light made incident on the respective light receiving faces Pa and Pb (FIG. 10) of the photodetectors 45a and 45b, compares the optical outputs with a reference value, for a collation thereof, and outputs a detection signal $V_L$ indicating whether the finger 40 is a genuine finger or a replica.

In FIG. 9, among the paths of light, shown as being reflected by the contacting portion of a finger which are transmitted to the respective light receiving faces of the photodetectors 45a and 45b, a light path indicated by a continuous line is that formed when the finger 40 is a non-biological object (a replica). Further, a region R of the finger 40 indicated by a broken line, causes the irradiated light is reflected and scattered due to a propagation and diffusion of the irradiated light in the finger, and this region appears only when the finger 40 is a biological object (a genuine finger). Therefore, in such a case, the center of the region R is displaced from the center of the originally irradiated portion, and accordingly, paths of light, as reflected by the genuine finger contacting portion and transmitted to the light receiving faces of the respective photodetectors 45a and 45b, will expand relatively in the cross sectional direction, as indicated by broken lines.

Figure 10:
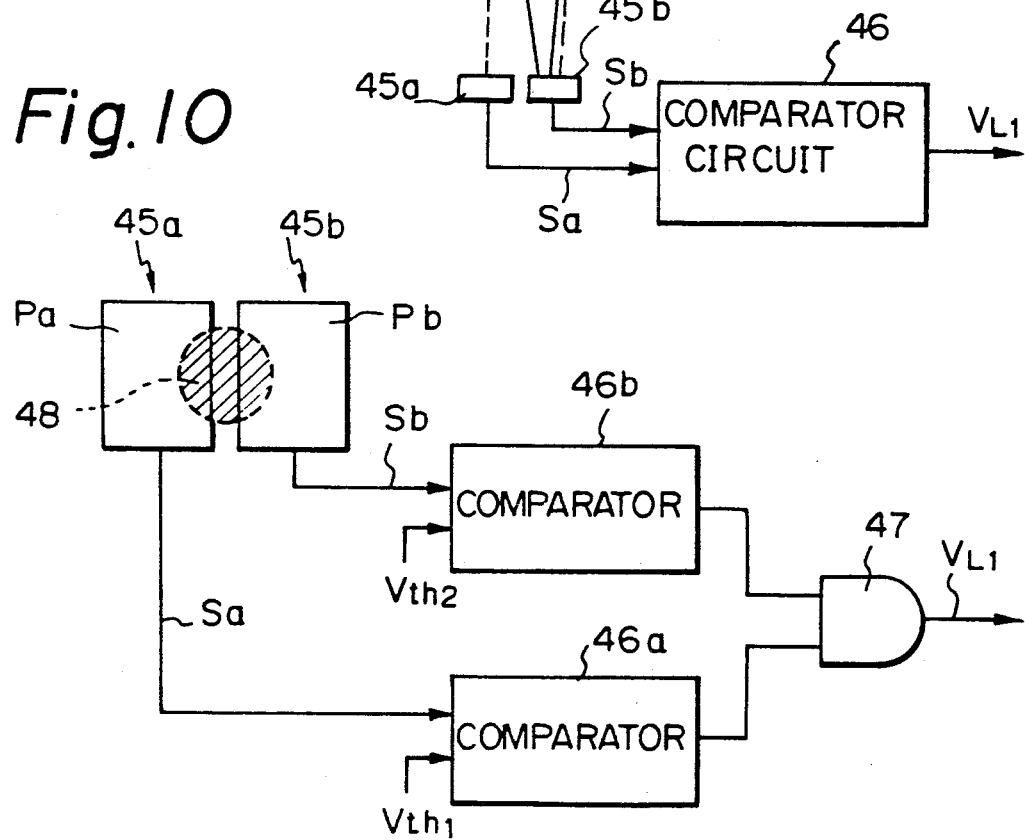
FIG. 10 is a circuit diagram showing a typical example of the photodetectors and comparator circuit shown in FIG. 9.

FIG. 10 shows typical examples of the photodetectors and comparator circuit shown in FIG. 9.

In FIG. 10, the photodetector 45a outputs an optical output Sa corresponding to an amount of light made incident on the light receiving face Pa, and this output Sa is input to a comparator 46a. The comparator 46a compares the level of the input signal Sa with a predetermined level $Vth_1$, and outputs a signal "1" if $Sa > Vth_1$ is satisfied, or if $Sa \leq Vth_1$ is satisfied, outputs a signal "0". Similarly, a comparator 46b compares the level of an optical output Sb that corresponds to an amount of light made incident on the light receiving face Pb of the photodetector 45b with the predetermined level $Vth_2$, and if $Sb > Vth_2$ is satisfied, outputs a signal of "1", or if $Sb \leq Vth_2$ is satisfied, outputs a signal "0". The outputs of the respective comparators are input to an AND gate 47.

Only when the amounts of light detected by the photodetectors 45a and 45b exceed the respective predetermined levels ($Vth_1$, $Vth_2$), does the AND gate 47 output the detection signal $V_{L1}$ as "1"; in all other cases, the detection signal $V_{L1}$ is output as "0".

A hatched portion 48 in the figure shows a typical image formed on the light receiving faces Pa and Pb of the respective photodetectors by the irradiated light reflected and scattered by the finger 40.

The operation (biological detection) of the embodiment shown in FIG. 9 will be explained with reference to FIG. 11.

Figure 11A:
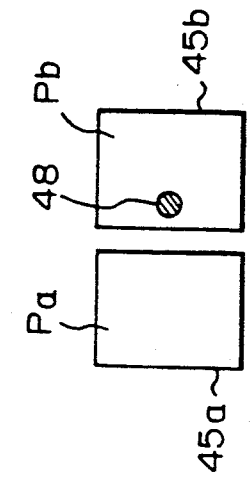
FIGS. 11A to 11D are views explaining the principle of the biological detection used in the embodiment of FIG. 9.
Figure 11B:
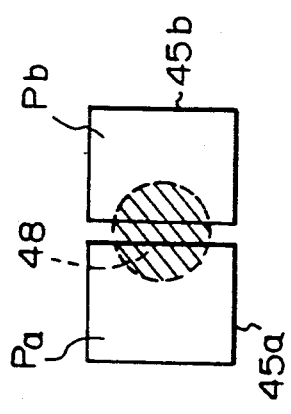
Figure 11C:
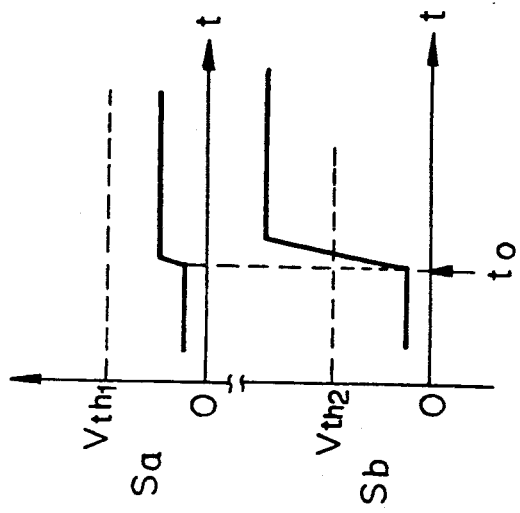
Figure 11D:
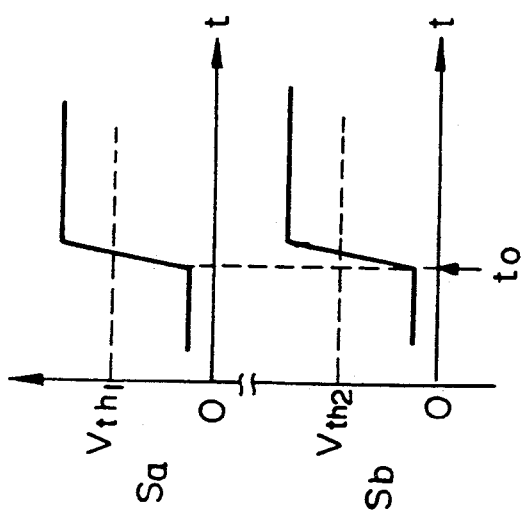

FIG. 11A shows the positional relationships of the image of a genuine finger and the light receiving faces, FIG. 11B shows the positional relationships of the image of a replica and the light receiving faces, FIG. 11C shows the relationship between the output levels Sa and Sb of the respective photodetectors of FIG. 11A and the threshold levels $V_{th1}$, $V_{th2}$, and FIG. 11D shows the relationship between the output levels Sa and Sb of the respective photodetectors of FIG. 11B and the threshold levels $V_{th1}$, $V_{th2}$. The time $t_0$ in each of FIG. 11C and FIG. 11D is the time at which the finger 40 touches a predetermined position on the light guiding board 43.

If the finger 40 is a genuine finger, the region R occurs in the finger 40 as described above, and therefore, a region at which light is reflected and scattered by the surface of the finger expands relatively as indicated by a broken line in FIG. 9. Accordingly, the image 48 shown in FIG. 11A extends over the light receiving faces Pa and Pb of the respective photodetectors, and therefore, the photodetectors 45a and 45b output the optical outputs Sa and Sb each having a certain level. In this case, if the levels of the optical outputs Sa and Sb are higher than the respective predetermined levels $V_{th1}$, $V_{th2}$, the outputs of the comparators 46a and 46b of FIG. 10 are "1", and thus the AND gate 47 outputs a detection signal $V_{L1}$ as "1" to indicate the detection of a biological object.

If the finger 40 is a replica, however, the region at which light is reflected and scattered by the surface of the finger is relatively focused as indicated by a continuous, or solid, line shown in FIG. 9, and therefore, the image 48 is formed on the light receiving face Pb of one of the photodetectors as shown in FIG. 11B. The light receiving face of the other photodetector receives only a little light, i.e., only a flared portion of the light focused on the light receiving face Pb, and therefore, the photodetector 45b outputs an optical output Sb having a certain level, and the photodetector 45a outputs an optical output Sa having a very low level. In this case, if the predetermined levels $V_{th1}$, $V_{th2}$ are set such that the level $V_{th2}$ is lower than the level of the optical output Sb and the level $V_{th1}$ is higher than the level of the optical output Sa, the detection signal $V_{L1}$ output from the AND gate of FIG. 10 will be "0", and accordingly, it is determined that the finger 40 is a replica.

In the embodiment of FIG. 9, the image 48 is formed in such a manner that it extends over both light receiving faces of the respective photodetectors when the sample is a genuine finger, and extends over only one of the light receiving faces when the sample is a replica. In the embodiment shown in the figures, the photodetector 45b determines that the finger 40 (a genuine finger or a replica) is in contact with the light guiding board 43, and the photodetector 45a determines whether or not it is a biological object.

As described above, according to the embodiment of FIG. 9, whether the signal $V_{L1}$ output from the comparator circuit 46 is 1 or 0 enables an instantaneous determination of whether the finger 40 is a genuine finger (a biological object) or a replica (a non-biological object). Similar to the system of FIG. 4, the system of FIG. 9 can be assembled in a fingerprint image input apparatus of a fingerprint collating system.

The embodiment of FIG. 9 uses two photodetectors 45a and 45b arranged adjacent to each other, but a solid type photodetector having a light receiving face divided into two regions each separately providing an optical output corresponding to an amount of light received by the corresponding region can be employed instead.

Figure 12:
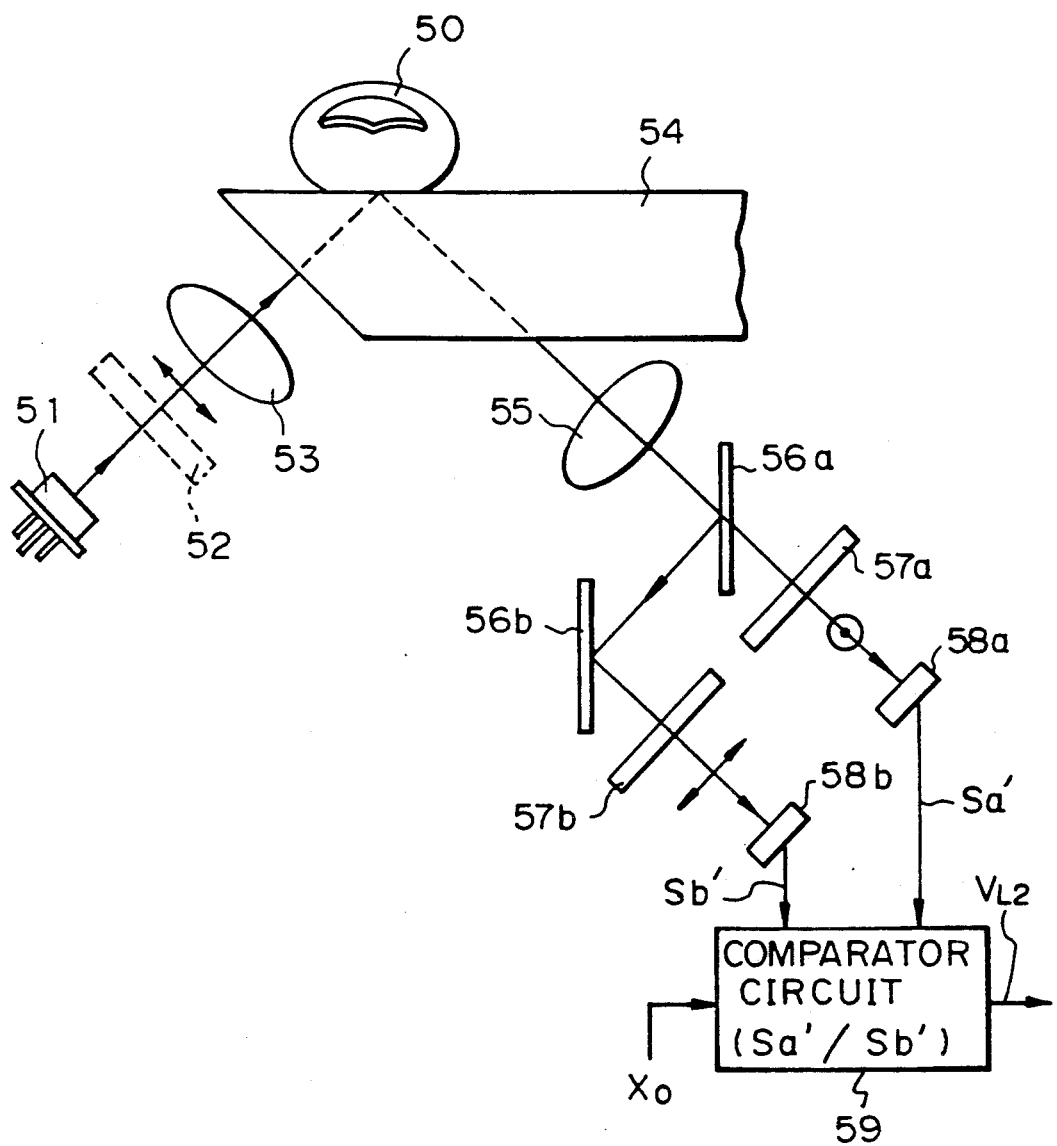
FIG. 12 is a view showing an embodiment according to the third aspect of the present invention shown in FIG. 3.

FIG. 12 shows an embodiment according to the third aspect (FIG. 3) of the present invention.

In FIG. 12, 50 denotes a finger (a genuine finger or a replica) as a sample; 51 a light source for biological detection, such as a semiconductor laser or an LED; 52 a polarizing plate which can be omitted if the light source 51 is a semiconductor laser) for linearly polarizing (in a direction parallel to the surface of the paper, according to the shown embodiment) a light beam from the light source 51; 53 a condensing optical system (a lens) for condensing the light beam from the light source 51 and irradiating the surface of the finger 50 with a spot of light; 54 a transparent light guiding board; and 55 an optical system (a lens) for condensing light reflected and scattered by the surface of the finger irradiated with the light beam.

Further, 56a denotes a beam splitter for dividing the scattered light beam incident on the lens 55, into two light beams while maintaining the polarization direction of the scattered light as it is; 56b a mirror for reflecting the light beam, split by the beam splitter 56a and incident thereon in a direction orthogonal to the direction of incidence thereof; 57a a polarizing plate for polarizing the scattered light passed through the beam splitter 56a in a predetermined direction perpendicular to the paper, according to the shown embodiment); 57b a polarizing plate for polarizing the scattered light reflected by the mirror 56b in a direction perpendicular to the polarization direction of the polarizing plate 57a (a direction parallel to the surface of the paper, according to the shown embodiment, i.e., the same direction as the polarization direction of the scattered light made incident on the lens 55); 58a a photodetector for detecting the light intensity of the polarized light polarized by the polarizing plate 57a and outputting an optical output Sa, corresponding to the light intensity; 58b a photodetector for detecting the light intensity of the polarized light polarized by the polarizing plate 57b and outputting an optical output Sb' corresponding to the detached light intensity; and 59 a comparator circuit. The comparator circuit 59 calculates the ratio of the optical outputs Sa' and Sb' output from the photodetectors 58a and 58b, compares the ratio (Sa'/Sb') with a predetermined value $X_0$, and outputs a detection signal $V_{L2}$ indicating whether the finger 50 is a genuine finger or a replica.

The operation (biological detection) of the embodiment of FIG. 12 will be explained with reference to FIG. 13.

Figure 13:
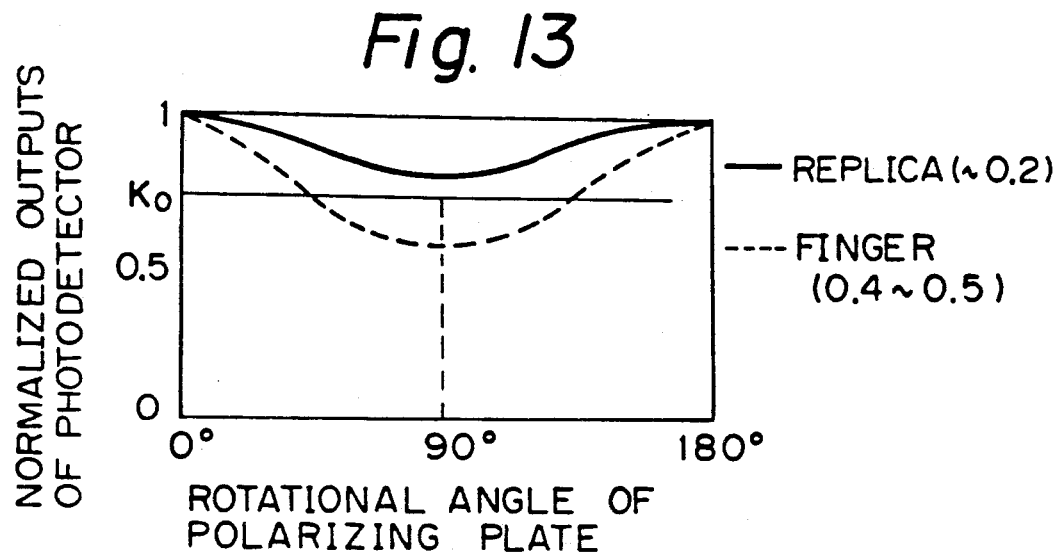
FIG. 13 is a view explaining the principle of the biological detection used in the embodiment of FIG. 12.

FIG. 13 shows a comparison of the characteristics of polarized light scattered from a genuine finger and from a replica. The abscissa of the figure represents an angle between the linear polarization direction of the irradiated light and the polarization direction of the polarizing plate, and the ordinate of the figure represents a value derived by normalizing outputs of the photodetectors with maximum outputs. FIG. 13 shows that the light scattered from the genuine finger provides a better preservation of the polarization direction of the irradiated light than does the light scattered from the replica. Namely, as shown by the example, the genuine finger preserves 40% to 50% of the polarization direction of light from a light source, but the replica preserves only up to 20% of the same. Therefore, after the comparator circuit 59 provides a ratio of the optical outputs Sa' and Sb' from the photodetectors 58a and 58b, a difference will be observed between the polarization disturbing characteristics of the genuine finger and of the replica.

As shown in FIG. 13, when the angle of rotation of the polarizing plate is 90°, the difference between normalized outputs of the photodetectors for the replica (indicated by a continuous line) and for the genuine finger (indicated by a broken line) will be a maximum value, and if the predetermined value $K_0$ is set within the range whether or not the finger 50 is genuine can be determined by comparing the normalized ratio (Sa'/Sb') calculated by the comparator circuit 59 with the predetermined value $K_0$, and by using the polarization disturbance characteristics; i.e., taking the polarization characteristics into account, the embodiment sets a difference between the polarization directions of the polarizing plates 57a and 57b at 90°. Similar to the systems shown in FIGS. 4 and 9, the system shown in FIG. 12 can be assembled in a fingerprint image input apparatus of a fingerprint collation system.

Figure 14:
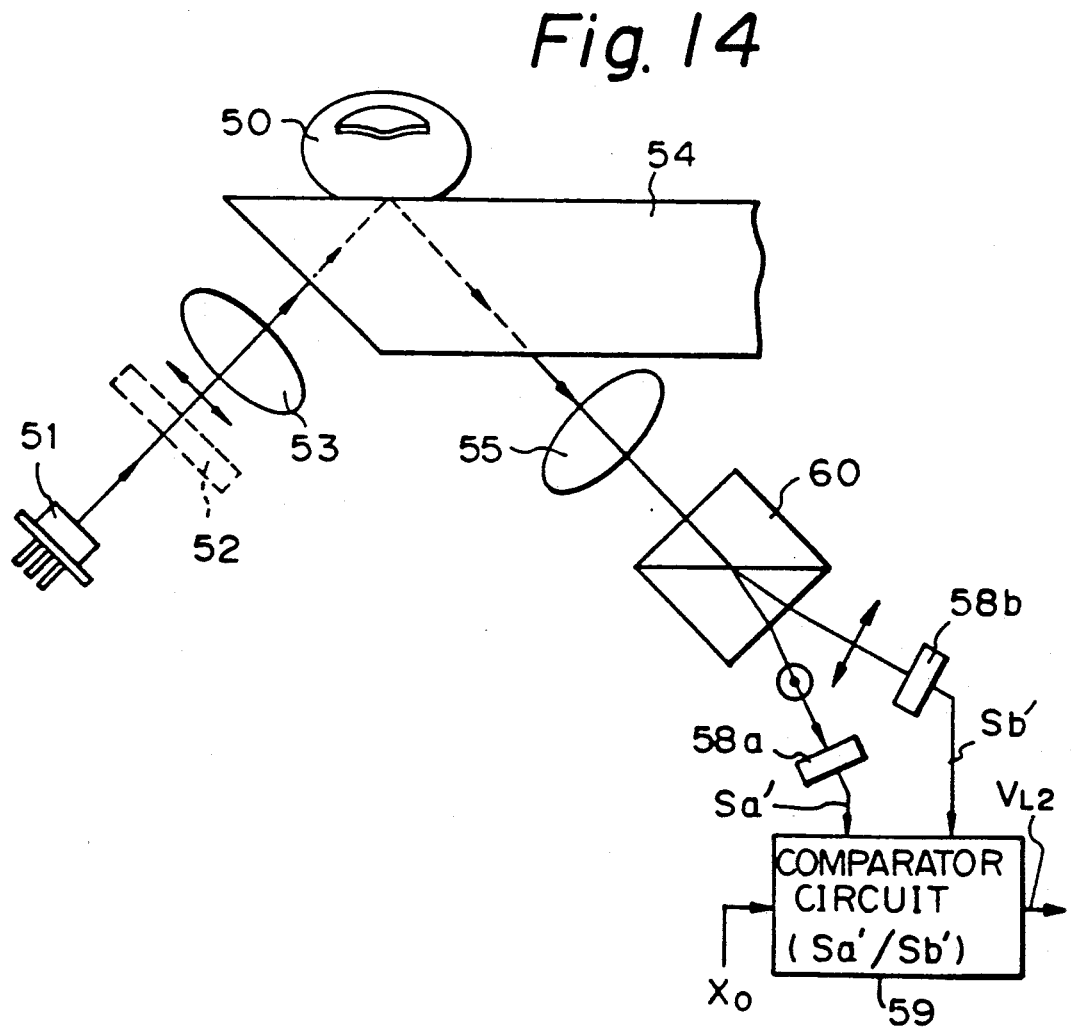
FIG. 14 is a view showing a modification of the embodiment of FIG. 12.

FIG. 14 shows the arrangement of a modification of the embodiment of FIG. 12.

Instead of the beam splitter 56a, mirror 56b, and polarizing plates 57a and 57b shown in FIG. 12, this modification employs a Wollaston prism 60 to form a polarizing optical system in which the number of optical parts, and thus the size of the system, is reduced. The other arrangements and operation are the same as those of the embodiment shown in FIG. 12, and thus an explanation thereof will be omitted.

Although the respective embodiments hereinabove are described as contact type fingerprint image input systems (biological detecting systems) employing light guiding boards, the invention also can be applied to non-contact type systems that do not employ the light guiding boards.

As described above, according to the present invention, the surface of a sample is irradiated with a spot of light or linearly polarized light, and the illumination occurring at the surface, or the polarization characteristics of light scattered from an irradiated portion of the sample, provide phenomena peculiar to the sample. The invention utilizes these phenomena or characteristics, peculiar to the material used as the sample, to instantaneously determine whether or not the sample is a biological object, without being influenced by the conditions of the sample; namely, as this invention utilizes characteristics peculiar to certain materials, the invention can improve the security of systems for detecting forged fingerprints.

Further, the present invention can detect a biological object within a short time, and thus the time needed by an identification apparatus to carry out the fingerprint collation can be shortened.

Furthermore, the invention can be assembled in both contact type and non-contact type fingerprint collation systems.

Figure 15:
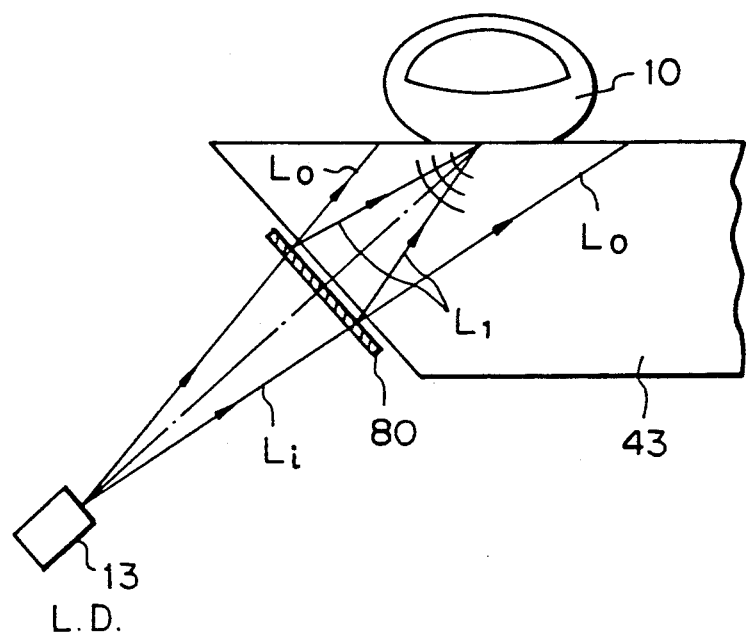
FIG. 15 is a view explaining the principle of a fingerprint input apparatus according to an embodiment of the present invention.

FIG. 15 shows another embodiment of the present invention, which uses a common light source as the light source for the fingerprint image input system and the light source for producing a beam spot for the biological detecting system, thus simplifying and reducing the weight of a fingerprint input apparatus.

According to this embodiment, a single illuminating means generates diverging waves that entirely illuminate a finger in addition to converging waves that partly illuminate the finger with a spot of light, and a grating lens 80 shown in FIG. 15 is employed for this purpose. The grating lens 80 is able to focus diverging waves supplied from a light source (for example, a laser diode LD) 41 at high efficiency. Among the diverging light waves or beams Li incidental to the grating lens 80, a zero-order transmitted light beam L0 maintains the state of the diverging waves thereby to widely illuminate the whole finger 10, and a first-order diffracted light beam L1 comes focused waves which partly illuminate the finger with a spot of light. With this arrangement, the single light source 41 can provide two kinds of light beams.

Figure 16:
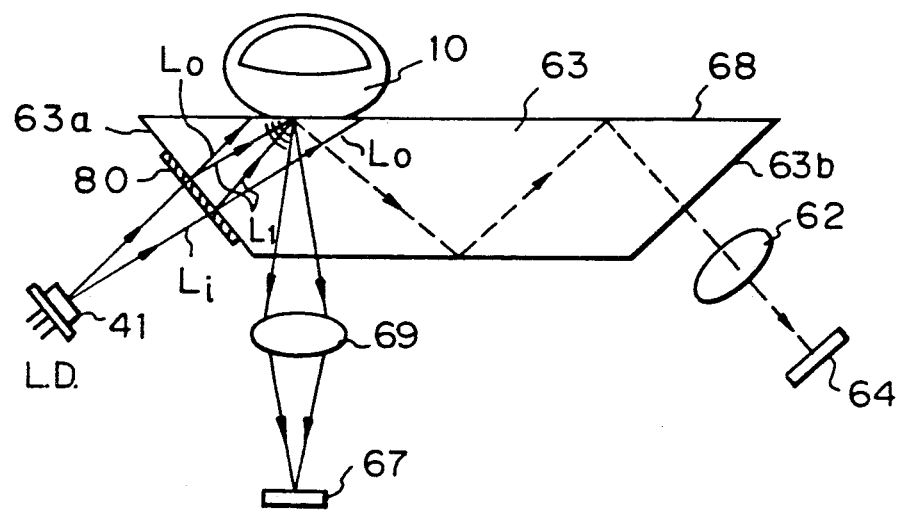
FIG. 16 is a view showing a more concrete embodiment of the apparatus of FIG. 15.

FIG. 16 is a more concrete embodiment of FIG. 15. The light source 41 is a laser diode, and a transparent light guiding board (transparent body) 63 has a diagonal cut portion 63a on which a grating lens 80 is formed, and the grating lens 80 focuses a laser light beams Li to provide a focused beam L1, and provides a transmitted light beams L0 for entirely illuminating a finger. Among the light beams scattered by the fingerprint contacting portion, components that propagate inside the light guiding board 63 due to the total reflection thereof are picked up from a diagonally cut face 63b and guided to an imaging system (lens) 62 to form an image of the finger on a CCD 64.

The principle of biological detection will be again described. When a replica made of silicon rubber, etc., is irradiated with a spot of light, light is scattered only in the close vicinity of an irradiated portion of the replica, and the size of an image of the irradiated portion is determined by the size of the irradiated light spot and the magnification of an imaging system. The spot image is formed on the photodetector 67 through the convergent lens system 69. If biological matter (i.e., a finger) is irradiated with light, however, the light penetrates the finger so that the light is scattered over a wide area of the finger, and therefore, the size of spot image formed on the photodetector 67 is larger than that formed by the replica. When the surface of the finger is obliquely irradiated with a spot of light, the center of the light scattering region of the finger is dislocated from that of the replica, and by detecting the size and center position of the spot image obtained from the scattered light, it is possible to carry out biological detection. The photodetector 67 may be a known divisional detector having a plurality of light receiving regions, or may comprise a plurality of small photodetectors arranged in an array.

Figure 17:
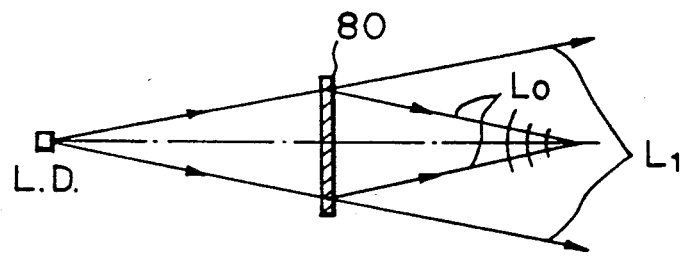
FIGS. 17 and 18 are views explaining the two ways of using a grating lens, respectively.
Figure 18:
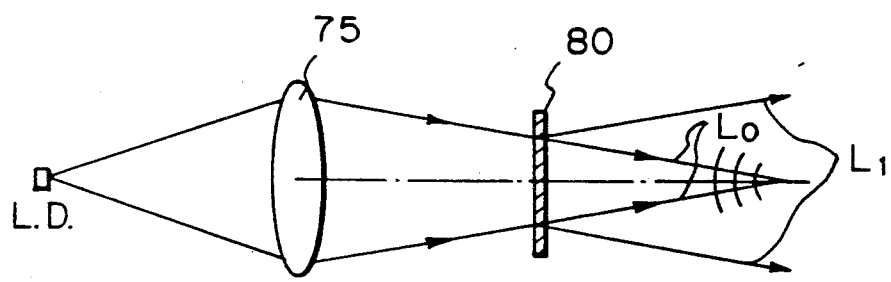

FIGS. 17 and 18 show two ways of using the grating lens 80. FIG. 17 uses a diverging beam wherein a zero-order transmitted light beam L0 entirely illuminates a finger and a first-order diffracted light beam L1 illuminates the contacting face of a finger with a spot of light. FIG. 18 uses a focusing beam in which a zero-order transmitted light beam L0 irradiates the contacting face of a finger with a spot of light and a first-order diffracted light beam L1 entirely illuminates the finger. If a diverging light source such as a semiconductor laser is employed, the case of FIG. 17 is preferable, but a converging lens system 75, as in FIG. 18 may used to enable an easy change over to converging light.

Figure 19:
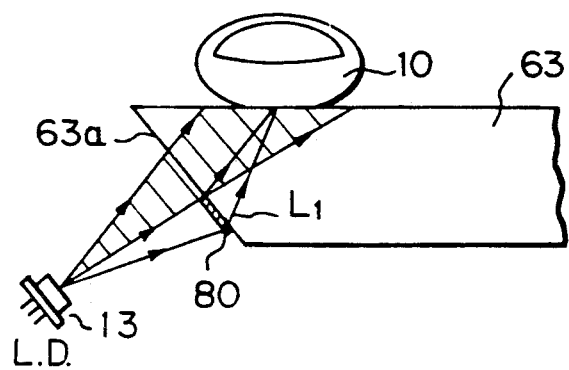
FIG. 19 is a view showing a modification of the embodiment of FIG. 16.
Figure 20:
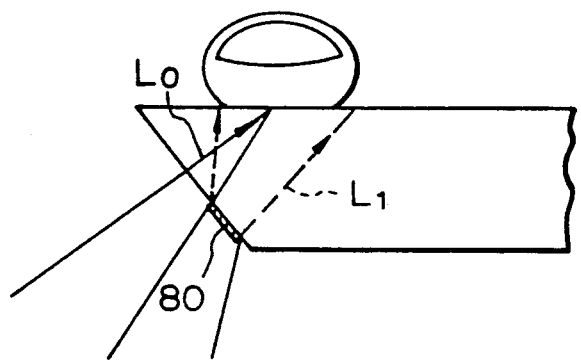
FIG. 20 is a view showing a modification of the embodiment of FIG. 19.

FIGS. 19 and 20 show two other embodiments of the invention, respectively. In FIG. 19, a light guiding board (transparent body) 63 has a diagonally cut portion 63a, on a part of which a grating lens 80 is formed. Part of the illuminating light (first-order diffracted light beam L1) is used to irradiated the finger contacting face with a spot of light, and light beam (hatched portion), that is made incident on the light guiding board 63 through a portion at which the grating lens 80 is not formed, entirely illuminates the finger.

Contrary to the case of FIG. 19, the case of FIG. 20 uses converging incident light. First-order diffracted light beam L1 forms diffused illuminating light, and a direct incident light beam L0, that does not pass through a grating lens 80, forms a spot of light. Part of the spot of light beam is a zero-order light transmitted from the grating lens 80.

The above-explained grating lenses are used to form a circular small spot of light, but it is possible to change a pattern of the grating lens to form, for example, an oval spot, to improve the detection sensitivity.

The grating lens may be formed integrally with the light guiding board, or may be formed separately from the light guiding board and then adhered to the light guiding board.

As described above, the embodiments employ a single grating lens for providing a light source for a fingerprint image input apparatus having a biological detecting function. The light source with the grating lens can provide light for entirely illuminating a finger contacting face to form an image of a fingerprint on an image sensor (CCD) and as a spot of light for biological detection for irradiating the finger contacting face. The invention is very effective when forming an illuminating system for a biological detection for a fingerprint image input apparatus that has no biological detecting function, without an increase in the volume and weight of the fingerprint image input apparatus.

Figure 21:
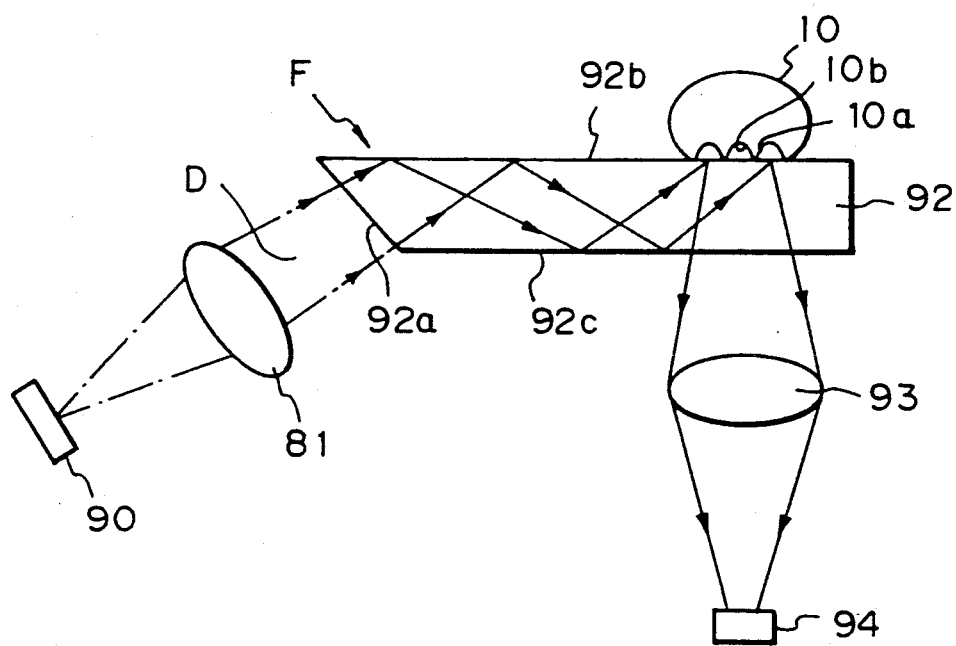
FIG. 21 is a schematic view of a biological discriminating system according to an embodiment of the present invention.

FIG. 21 shows still another embodiment of the present invention. For better understanding same, reference is first made to FIG. 35.

In the total reflection type biological discriminating system shown in FIG. 35, light that irradiates the grooves of a fingerprint is totally reflected by the grooves because the grooves form total reflection faces, and as a result, even if the sample is a biological object, it may be erroneously recognized as a replica.

Accordingly, the embodiment shown in FIG. 21 provides a biological discriminating system that sets the irradiating width of light, so that its capacity for discriminating a replica from a biological subject is enlarged.

In FIG. 21, a numeral 90 is a light source (LD), and light from the light source 90 is adjusted to a preferable spread by a condensing optical system (lens) 81. Here, the term preferable spread means that the width of the light beam irradiated on an interface (F) becomes wider than the mean gap between ridges of a fingerprint. The spread adjusted light may be coherent light or gradually focused light beam. A light D adjusted by the condensing optical system 81 is made incident on a slanting face 92a of a light guiding board (transparent body) 92. The light guiding board 92 is made of transparent material such as glass and is supported in air. An incident angle of the light beam D is such that a perpendicular line of the slanting face 92a coincides with the optical axis the light beam D, and therefore, most of the light beam D passes through the light guiding board 92 and reaches one face 92b of the light guiding board 92. An incident angle of the light beam with respect to the one face 92b is such that the angle exceeds a critical angle determined by the refractive index of the light guiding board 92 and the refractive index of air, and thus light that enters the one face 92b with an incident angle exceeding the critical angle is totally reflected by the interface (F) between the light guiding board 92 and air. The totally reflected light is totally and repeatedly reflected between the one face 92b and the other face 92c, which is parallel to the one face 92b, and thus the reflected light moves forward inside the light guiding board 92, is emitted from the light guiding board 12, and is condensed by an imaging optical system 93 to form an image on a photodetector 94.

The surface of the finger 10 defines a fingerprint comprising ridges 10a and grooves 10b.

Generally, the gap between the ridges 10a varies depending on the pattern and position of the fingerprint, but the gap never exceeds 1 mm; i.e., almost all of the gaps are each smaller than 1 mm. The embodiment sets the width of a spot of light, totally reflected by the one face 92b (identical to the interface (F)), to be wider than the gap between the ridges. Namely, if the gap between the ridges is, for example, 1 mm, a concrete value of the width of a spot of light is larger than 1 mm.

With this arrangement, the finger 10 is pressed against the one face (detection surface) 92b and a total reflecting face is not formed between the face 92b and the (ridges 10a) of the finger 10, and thus part of the light is propagated along a lower part of skin of the finger 10 and is irregularly reflected thereby. Accordingly, illumination occurs at a periphery of a portion of the surface of the finger 10 directly irradiated with the light, and the illuminated portion of the finger becomes larger than the portion irradiated with the light.

If the sample is a replica made of, for example, silicon based rubber, illumination occurs only in an area which is in close vicinity to the spot of the replica which is irradiated with light, so that the illuminated portion of the replica is smaller than that of the finger, i.e., biological object. Therefore, by observing a difference between the illuminated areas by the photodetector 94, it is possible to determine whether or not the sample is a biological object.

A position of the finger 10 on the light guiding board may vary, and according to this embodiment, the width of a spot of light irradiated on the face 92b (F) is wider than the gap between ridges of a fingerprint, so that even if the position of the finger is displaced, one ridge (projection 10a) is always inside the spot of light. Therefore, illuminated around the ridge is always correctly observed and thus the biological discrimination is carried out without hindrance and the discrimination improved.

Figure 22:
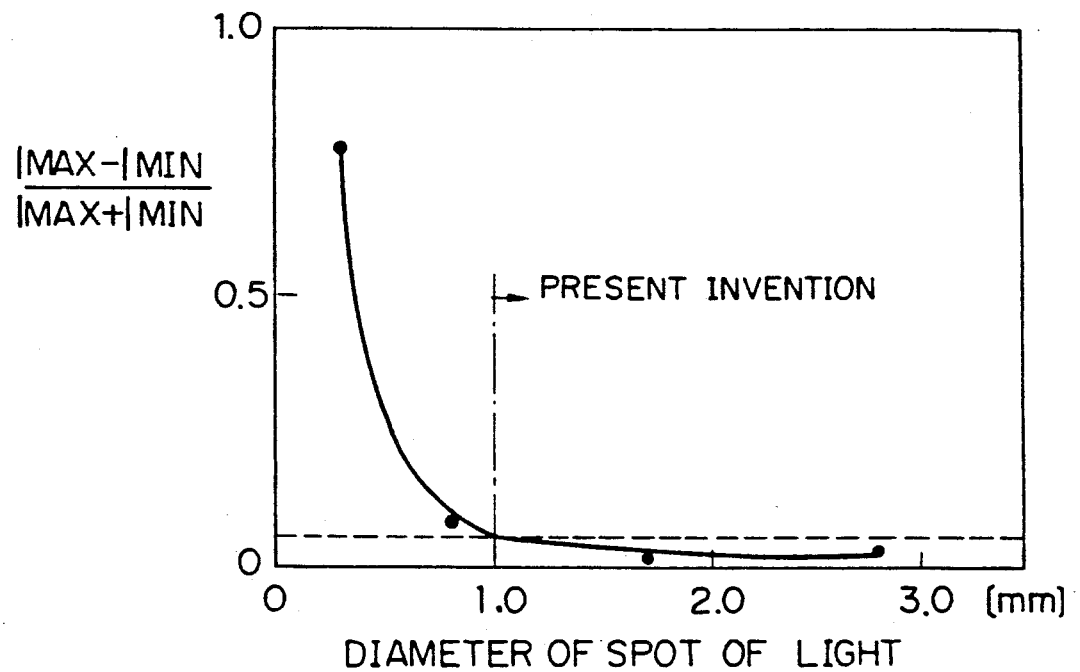
FIG. 22 is a graph showing the relationship between the diameter of spots of light and reflection tendency values.

FIG. 22 is a graph showing the relationship between diameters of light spots and the reflection tendency values. In the graph, the reflection tendency values are expressed by the following equation (1)

$$(Imax - Imin) / (Imax + Imin) \qquad (1)$$

where, Imax is a value corresponding to a maximum value of reflected light quantity or level, and Imin is a value corresponding to a minimum of reflected light quantity or level.

Namely, when the reflection tendency value is large, the diameter of a spot of light is less than 1 mm and thus the grooves and ridges of a fingerprint are irradiated with different spots of light. Accordingly, if a finger is displaced even slightly under this state, the quantities of reflected light will greatly vary. On the other hand, if the diameter of a spot of light is larger than 1 mm, the reflection tendency value is small so that quantities of reflected light are not drastically varied. Therefore, by enlarging the diameter of a spot of light to a value greater than 1 mm, a satisfactory reflected light beam is always obtained from the surface of a finger even if the finger is slightly displaced, thereby affording accurate biological discrimination.

According to the embodiment, a spot-like irradiating light is emitted to the face 92b (F), and the diameter of the spot is set.

Figure 23:
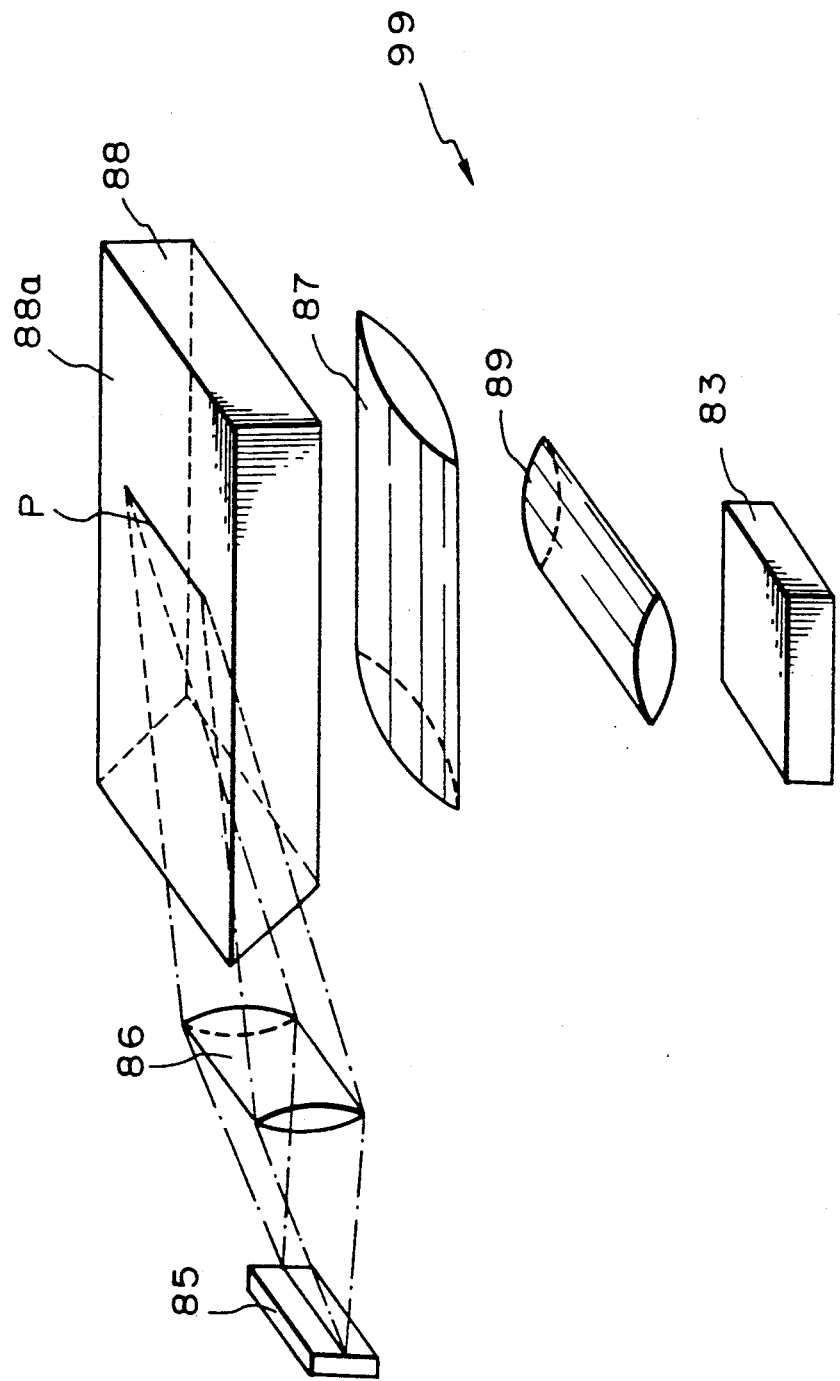
FIG. 23 is a schematic view of a biological discriminating system according to another embodiment of the present invention.

FIG. 23 shows another embodiment of the invention, which utilizes linear light for the irradiation, and wherein the width of the irradiating light beam is set. In FIG. 23, 85 is a light source for emitting linear light, 86 a cylindrical lens, and 88 a light guiding board (transparent body). Linear light P having a length exceeding a gap between the ridges of a finger is irradiated on one face (detection surface) 88a of the light guiding board 88 through the cylindrical lens 86. Numeral 99 is a photodetector portion comprising cylindrical lenses 87 and 89 and a photodetector 83.

Figure 24:
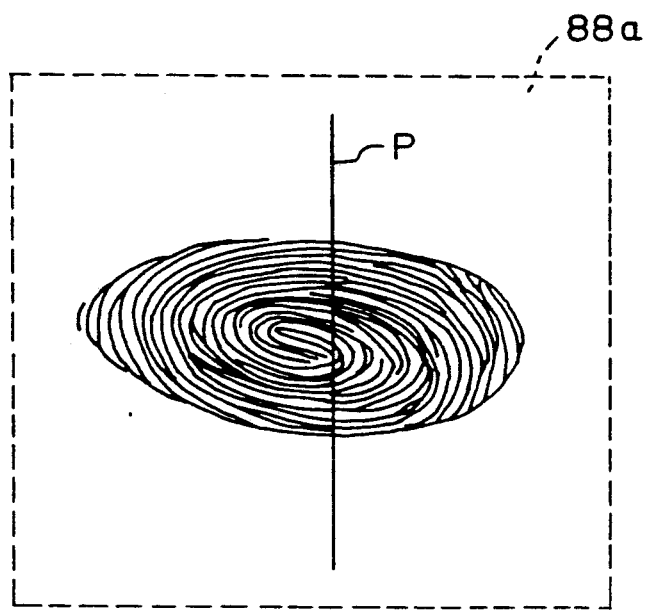
FIG. 24 is a view showing the relationships between the linear light P and a finger.

With this arrangement, a finger as a sample is pressed against the one face 88a of the light guiding board 88 and then, as shown in FIG. 24, the surface of the finger is irradiated with the linear light P. The length of the light P exceeds a gap between ridges of a fingerprint of the finger, so that one or more ridges of the fingerprint are irradiated with the light to carry out the biological discrimination without hindrance. Therefore, this embodiment can provide the same effect as the first embodiment.

According to this embodiment, the width of light irradiated on an interface is wider than the gap between the ridges of a fingerprint, so that the surface of a finger, i.e., ridges of fingerprint of the finger, are always irradiated with the light. Therefore, illumination around-!the ridges can be always observed, to improve the biological discrimination capacity.

Figure 25A:
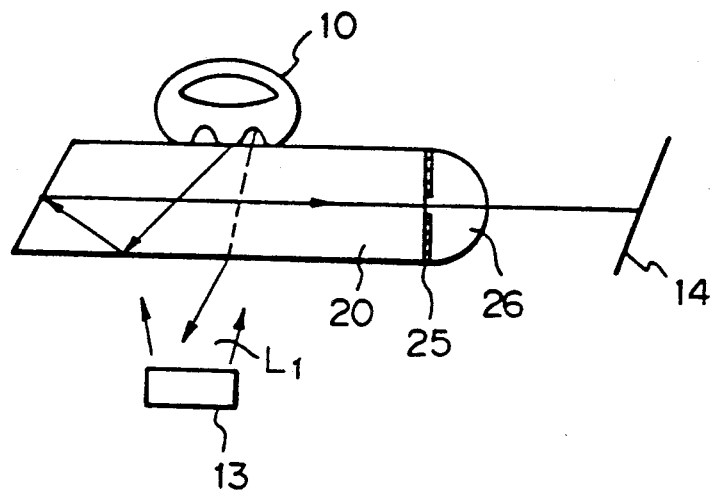
FIGS. 25A and 25B are views showing a principle of a fingerprint image input apparatus according to an embodiment of the present invention.
Figure 25B:
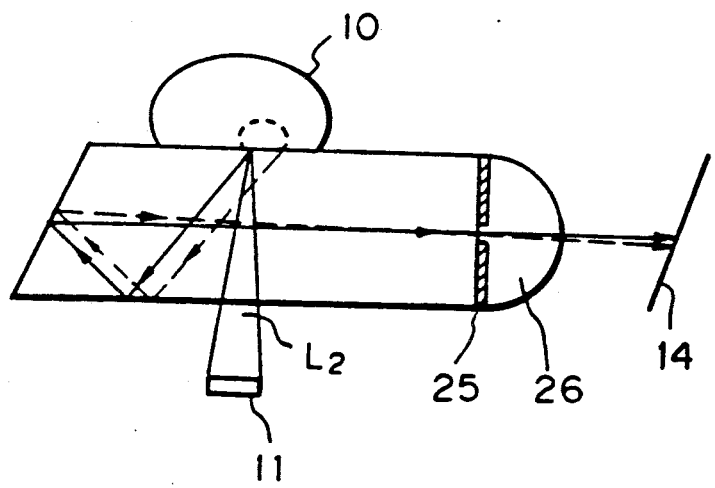

FIGS. 25A and 25B show another embodiment of the present invention in which the biological detection and the image detection are effected by one common optical system. In the arrangement for example, shown in FIG. 9 or FIGS. 4A–4C, the spot image reflected by the finger 40 or 10 is focused on the photodetector 45b or 12 (CCD) through the lens 44 or 22a. Namely, in the arrangement shown in FIG. 9, the special optical system for the biological detection including the lens 44 and the photodetectors 45a and 45b, etc., is provided in addition to the optical system for detecting the image of the fingerprint (not shown in FIG. 9). To reduce the number of the optical elements, the optical system for the biological detection is made common to the optical system for the image detection in FIGS. 25A and 25B. In the image detecting optical system shown in FIGS. 25A and 25B, the light beam L1 emitted from the LED 13 is incident upon the finger 10, so that an image of the finger 10 is focused on the CCD 14 through the fingerprint image forming means including the lens 26 and the diaphragm 25, to be detected thereby. This image detecting optical system is also used to perform the biological detection; namely, the light beam L2 in the form of a beam spot emitted from the laser diode 11 is incident upon the finger 10, so that a spot image reflected by the incident point of the light upon the finger 10 is focused on the CCD 12 (FIG. 25B) through the fingerprint image forming means including the lens 26 and the diaphragm 25, to be detected thereby. The biological detection itself can be effected in various ways (detection of the size or position of the spot image, etc. as mentioned above), and with this arrangement, the optical system for the biological detection can be omitted.

Figure 27:
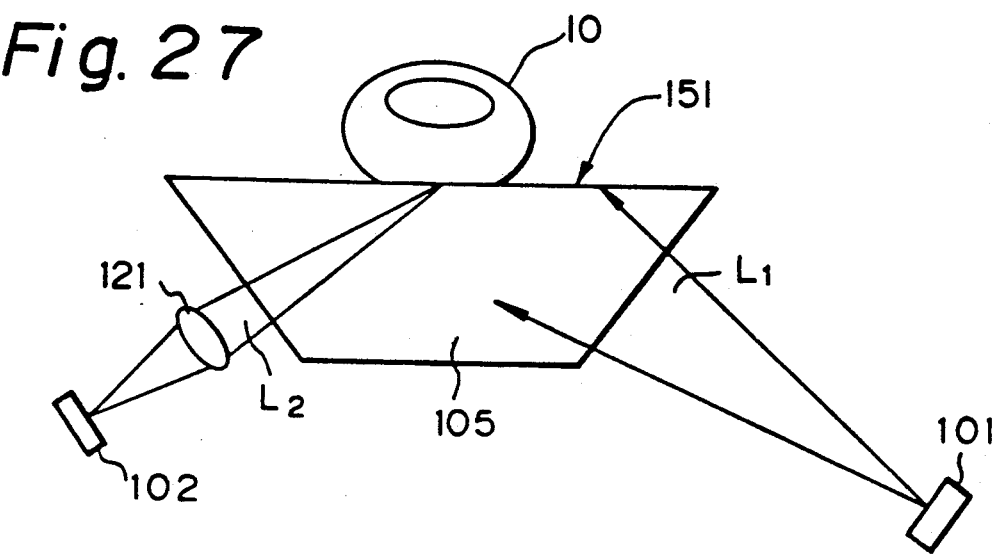
FIG. 27 is an enlarged view of a part of FIG. 26.

FIGS. 26 and 27 show an embodiment which utilizes an optical arrangement based on the principle shown in FIGS. 25A and 25B.

The fingerprint image input device includes a transparent body (transparent light guiding element) 105, a light source (LED) 101 for wholly illuminating the surface of the finger 10, a light source (laser diode) 102 for illuminating the finger 10 with a spot beam L2 to effect the biological detection, and a fingerprint image forming optical system 103 having the lens 131 and the (CCD) 104. The transparent body 105, which is made of a light permeable material such as glass, has a detection surface 151 on which the finger 10 is located, and the lens 131 is made integral with the transparent body 105 through the diaphragm 32 at one end of the transparent body 105. The light (fingerprint image and spot image) is converged onto the image detector 104, such as a CCD. The transparent body 105 is provided on the opposite end thereof with a mirror 152, to reflect the light reflected by the finger 10 toward the lens 131. The diaphragm 132 is a fixed diaphragm used to reduce possible aberration of the lens 131. This construction is substantially the same as that of the previously described embodiments.

The image obtained by the photodetector 104 is sent to a collating circuit 108 through an image fetching circuit 107, and to a biological detecting circuit 106. The biological detecting circuit 106 is provided with a designated address output detecting circuit 162 and a video signal output comparing circuit 162, to perform the biological detection.

The light source 101 for detecting the image of the fingerprint and the light source 102 for the biological detection are located below and on opposite sides of the transparent body 10, as can be seen in FIG. 27, so that the lower portion of the finger brought into contact with the detection surface 151 is totally illuminated, i.e., light L1 emitted from the light source 101 illuminates the whole surface of the finger 10. On the other hand, light L2 emitted from the light source 102 and converged by the lens 121 in the form of a beam spot is made incident on a point of the finger 10. The light sources 101 and 102 are constructed so that light is not emitted simultaneously thereby onto the finger 10. For example, the spot light beam is first instantaneously (e.g. less than a few msec.) emitted from the light source 102 to detect whether or not the finger is a genuine biological object, and light beam L1 is then emitted from the light source 101 to wholly illuminate the finger 10 to detect the fingerprint image, only when a real finger is detected.

The following discussion will be directed to the process of inputting the fingerprint image, with reference to FIGS. 25A and 26, which process is similar to that of the above-mentioned embodiments.

In the fingerprint image input apparatus of the illustrated embodiment, the light component of the light scattered from the ridges (projecting portion) of the fingerprint that is totally reflected by the critical surface of the transparent body 105 is converged onto the photodetector (CCD) 104 by the lens 131 to form an image of a pattern of the ridges of the fingerprint. Namely, the finger 10 brought into contact with the detection surface 151 of the transparent body 105 is wholly illuminated with light L1 emitted from the light source 101, so that the image of the ridges of the fingerprint can be detected by the photodetector 104.

When the finger 10 is pressed onto the detection surface 151 of the transparent body 105, the ridges of the fingerprint come into contact with the detection surface but the grooves (recessed portions) of the fingerprint do not come into contact with the detection surface 151, so that light incident on the finger through the transparent body 105 is reflected by the surface and the inside portion of the finger 10. Namely, since light scattered from the grooves of the fingerprint passes through the air and then enters the transparent body 15, a light component which is totally reflected in and transmitted through the transparent body 105 to the lens 131 does not exist. Nevertheless, the scattered light reflected by the ridges of the fingerprint directly enters the transparent body 105 without passing through the air, so that part of this light meets the total reflection condition in the transparent body 105. As a result, the light which meets the total reflection condition in the transparent body 105 repeatedly undergoes total reflection therein, and thus reaches the lens 131 through the diaphragm 132. The total reflection light component is focused onto the photodetector 104 by the lens 131 to form an image of the ridge pattern of the fingerprint.

The biological detection itself has been discussed.

Figure 28:
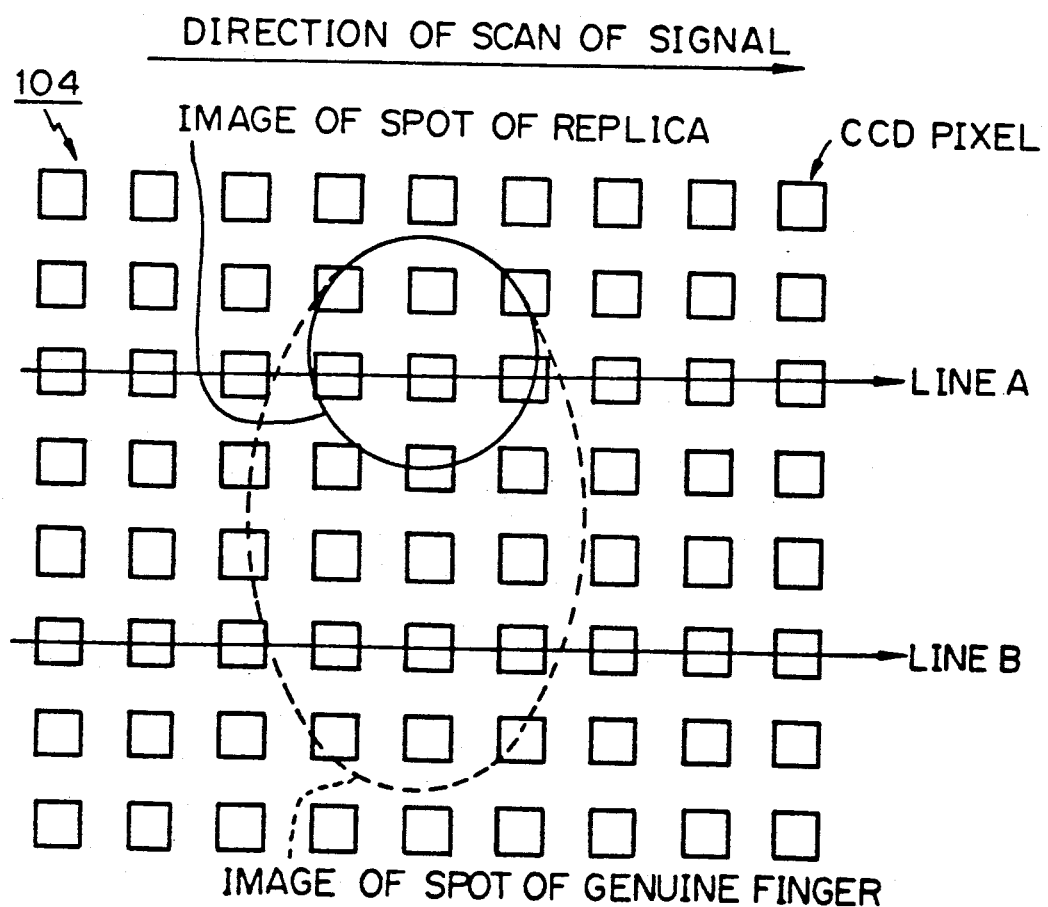
FIG. 28 is an explanatory view of a photodetector (CCD) used in the apparatus shown in FIG. 26.

As shown in FIG. 28, which shows the processes in the fingerprint image input apparatus, in the case of a genuine finger, when the beam spot is incident on the surface of the finger 10, not only is the illuminating point of the finger brighter, but also the circumferential portion is brighter, since the light is propagated and scattered in the finger 10, as mentioned before. As a result, the spot image of a genuine finger, as detected by the photodetector 104 occupies a relatively large area of the photodetector, as shown by an imaginary line in FIG. 28.

Conversely, in the case of a replica, when the beam spot is incident on the finger, only the incident point of the finger and the close vicinity thereof reflect or scatter the incident light and become brighter, and thus the spot image detected by the photodetector 104 occupies a very limited small area of the photodetector 104, as shown by a solid line in FIG. 28.

Figure 29:
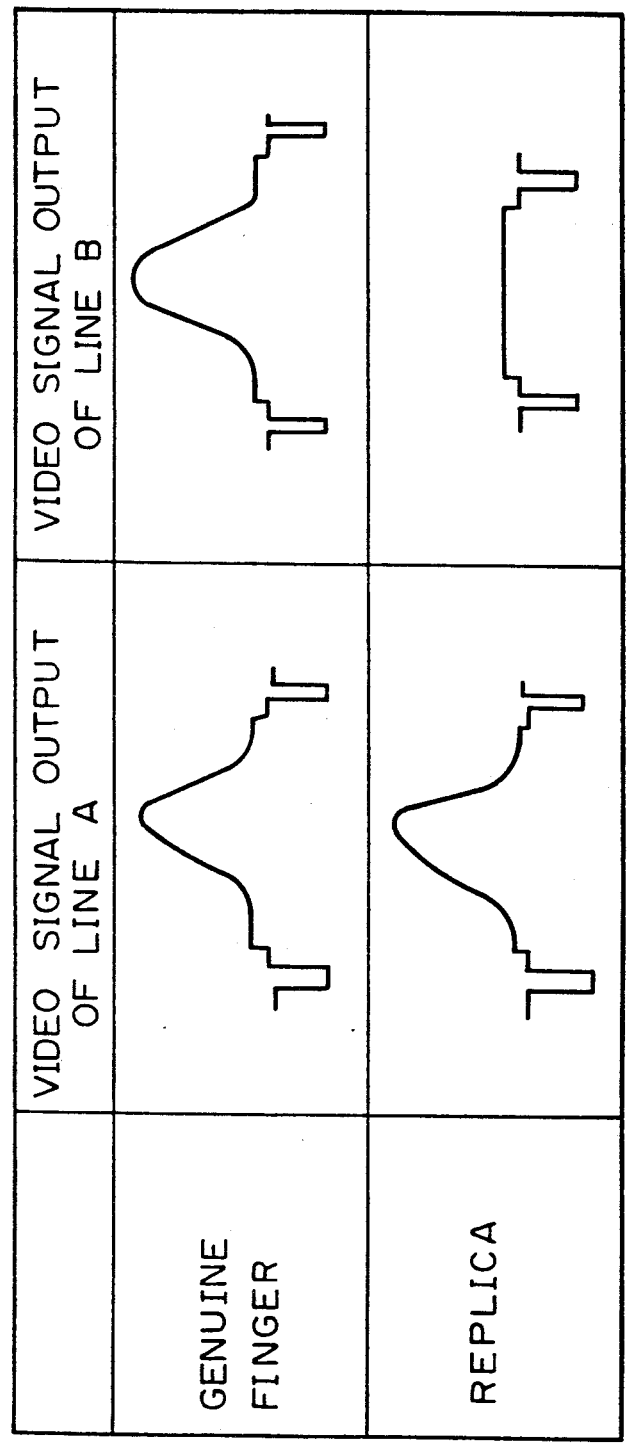
FIG. 29 is a schematic view of shapes of video signal outputs of lines A and B shown in FIG. 28.

FIG. 29 shows the shapes of video signal outputs of detectors along the lines A and B shown in FIG. 28.

As can be seen from FIG. 29, in the case of a replica, the video signal output changes only at the line A in the close vicinity of the incident point, whereas in the case of a genuine finger, the video signal output changes at both the lines A and B, which also cover the circumferential portion of the incident point. Namely, the spot image obtained by the photodetector 104 is supplied to the biological detecting circuit 106 shown in FIG. 26, so that the designated address outputs corresponding to the lines A and B predetermined by the designated address output detecting circuit 161 can be detected. Thereafter, for example, the designated address outputs of the lines A and B in the spot image are sent to the video signal output comparing circuit 162 to be compared. Namely, as can be seen in FIG. 29, when only the video signal output of the line A varies (i.e., a spot image exists only at the line A), the object is determined to be a replica. Conversely, when the video signal outputs of the lines A and B change (i.e., spot images exist at both the positions of the lines A and B), the object is determined to be a genuine finger.

It should be appreciated that the designated address output detected by the designated address output detecting circuit 161 is not limited to the two lines A and B. Furthermore, no restriction is made on the linear scanning of the output of the photodetector 104. That is, it is possible to check whether or not a plurality of linear outputs detected by the photodetector 104 include a spot image, i.e., whether or not the video signal outputs have changed. Alternatively, it is possible to designate a specific area of the photodetector 104 to check whether or not each picture element (pixel) of that area contains a spot image. Consequently, the subject located on the detecting surface 151 of the transparent body 105 can be discriminated to be a replica or a genuine finger by measuring the size and position, etc., of the image of the incident point detected by the photodetector 104, as mentioned before.

The phenomenon whereby, when a spot beam is incident upon a finger the beam penetrates the finger and is dispersed, is peculiar to human beings, and it is impossible to produce a replica having the characteristics of the genuine finger as mentioned above, at least by known techniques. Even if a user tries to disassemble the fingerprint image input device of the invention, since neither a special optical system for a biological detection nor a photodetector exist, it is difficult or next to impossible to figure out the biological detecting system incorporated therein, thus resulting in the maintaining of a secure system.

Figure 30:
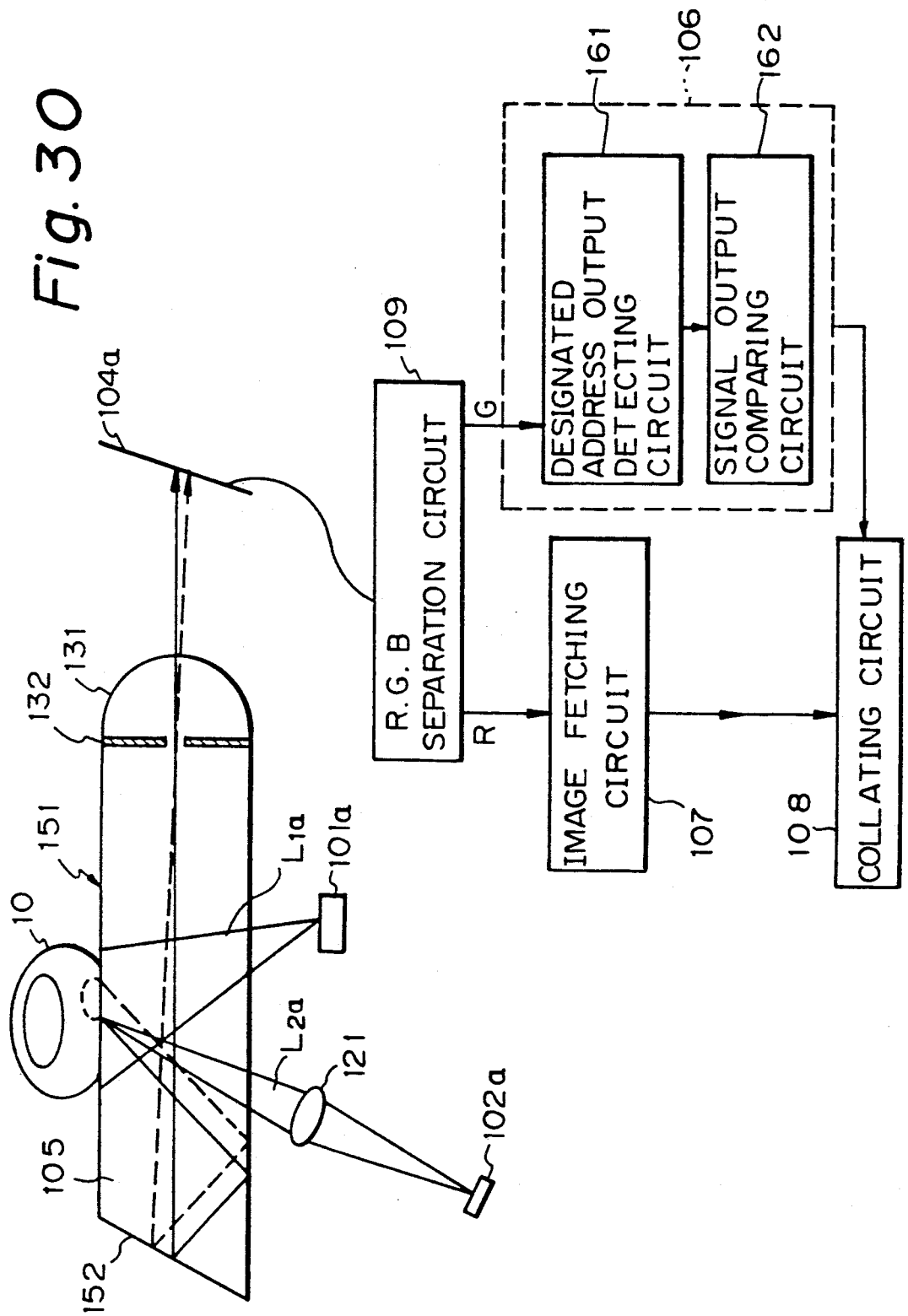
FIG. 30 is a view similar to FIG. 26 according to another embodiment of the present invention.

FIGS. 30 and 31 show another embodiment of the present invention. In the illustrated embodiment, the light source 101 (laser diode) for detecting the fingerprint image and the light source 102 (laser diode) for the biological detection shown in FIG. 26 are replaced by a light source 101a which emits a red light (R) and a light source 102a which emits a green light (G), respectively. In addition, the photodetector 104 in FIG. 26 is replaced by a color CCD 104a. The photodetector 104a is additionally provided with an R, G, B separation circuit 109, which separates the colors R, G, and B. Note that the light sources 101a and 102a are provided on opposite sides of the finger and below the transparent body 105, so that the lower surface of the finger 10 located on the detection surface 151 can be illuminated with beams of light from the light sources at one time.

The red light R of beam $L_{19}$ from the light source 101a wholly illuminates the finger 10, so that the light component of the light which is dispersed from the ridges of the fingerprint and totally reflected by the critical surface of the transparent body 105 is converged onto the photodetector 104a by the optical lens 131 to obtain an image representing a pattern of ridges of a fingerprint. Since the image of the ridge pattern of the fingerprint possesses a red color component R, the image signal corresponding to the red color R is separated by the R, G, B separating circuit 109 to be sent to the image fetching circuit 107, and the fingerprint collating process is performed in the collating circuit 108.

On the other hand, the green light G from the light source 102a is condensed by the lens 121 to be incident on the finger in the form of a spot beam $L2a$, to effect the biological detection mentioned above. Namely, the spot image reflected by the illumination point of the light beam $L2a$ is detected by the photodetector 104a, which is also used as a detector of the image of the fingerprint, through the lens 131. Since the spot image used for the biological detection possesses the green component G, the green image signal in the photodetector 104a is separated by the R, G, B separating circuit 109 to be fed to the designated address output detecting circuit 161 of the biological detecting circuit 106, so that the subject located on the detecting surface 151 can be determined to be a replica or a genuine finger by the signal output comparing circuit 162. Note, obviously the colors of the light emitted from the light sources 101a and 102a are not limited to red R and green G.

According to the embodiment illustrated in FIGS. 30 and 31, since the light beams L1a and L2a for detecting the fingerprint and for the biological detection can be simultaneously emitted from the respective light sources 101a and 102a, a faster detection rate can be obtained in comparison with the embodiment shown in FIGS. 26 and 27 in which the light for the biological detection must be emitted immediately before the emission of the light for the detection of a fingerprint image, as mentioned before.

With the arrangements shown in FIGS. 26 through 31, the biological detection can be effected by the same optical system which is used to detect the image of a fingerprint, and accordingly, a smaller number of optical components are needed, to thereby realize a simplified fingerprint image input apparatus. Furthermore, since a special optical system for the biological detection is not provided, it is almost impossible to determine how the system operates, even when disassembled.

We claim:

1. A biological object detecting system comprising:
 means for presenting the surface of a sample for optical scanning and detection as a biological sample;
 a light source for producing a light beam;
 condensing optical means for condensing the light beam from the light source and irradiating the surface of a sample to be detected with a light beam spot;
 imaging optical means for condensing light reflected and scattered by the irradiated portion of the sample and forming an image of the irradiated portion at a predetermined location; and
 photodetector means disposed at the predetermined location for detecting the size of the image of the irradiated portion and, correspondingly, for indicating whether the sample is a biological object or a replica, the photodetector means further comprising:
  a photodetector having a light receiving face disposed at the predetermined location, the face being defined by three adjacent light receiving regions producing respective, independent electrical signal outputs corresponding to the respective levels of light incident thereon, the second region being intermediate the outer, first and third regions, and the imaging optical means forming the image of the irradiated portion of the sample on the light receiving face of the photodetector,
  a first operational amplifier having a gain k and receiving the respective electrical outputs of the first and third light receiving regions and in response thereto producing an output k ($S_1+S_3$),
  a second operational amplifier receiving the output of the second light receiving region and of the first operational amplifier and, in response thereto, producing the output, and
  means for determining whether the sample is a biological object or a replica thereof in accordance with the output having a positive or negative value, respectively.

2. A biological object detecting system comprising:
 means for presenting the surface of a sample for optical scanning and detection as a biological sample;
 a light source for producing a light beam;
 condensing optical means for condensing the light beam from the light source and irradiating the surface of a sample to be detected with a light beam spot;
 imaging optical means for condensing light reflected and scattered by the irradiated portion of the sample and forming an image of the irradiated portion at a predetermined location; and
 photodetector means disposed at the predetermined location for detecting the size of the image of the irradiated portion and, correspondingly, for indicating whether the sample is a biological object or a replica, the photodetector means further comprising plural photodetectors having respective light receiving faces disposed in adjacent relationship at the predetermined location and producing respective, independent electrical output signals corresponding to the respective levels of light incident thereon, and the imaging optical means forming the image of the irradiated portion of the sample on the light receiving surfaces of the plural photodetectors; and
 means responsive to the independent electrical outputs signals for detecting the size of the image and correspondingly indicating whether the sample is a biological object or a replica.

3. A biological object detecting system comprising:
 means for presenting the surface of a sample for optical scanning and detection as a biological sample;
 a light source for producing a light beam;
 condensing optical means for condensing the light beam from the light source and irradiating the surface of a sample to be detected with a light beam spot;
 imaging optical means for condensing light reflected and scattered by the irradiated portion of the sample and forming an image of the irradiated portion at a predetermined location; and
 photodetector means disposed at the predetermined location and receiving thereon the image of the irradiated portion of the sample, for detecting whether or not the center of a region of the sample, at and within which the irradiating light beam is reflected and scattered, is displaced from the center of the directly irradiated portion of the sample and producing a detection output signal indicating the size of the image and whether the center of the region is, or is not, displaced from the center of the directly irradiated portion and correspondingly, that the sample is a biological object or is not a biological object and only a replica thereof.

4. A biological object detecting system according to claim 3, wherein the photodetector means comprises:
 plural photodetectors having respective light receiving faces disposed in adjacent relationship at the predetermined location and producing respective, independent electrical output signals corresponding to the respective levels of light incident thereon, said imaging optical means forming the image of the irradiated portion of the sample on the light receiving surfaces of the plural photodetectors; and
 means for comparing the output signals of the plural photodetectors with respective, different predetermined reference levels and thereby producing the detection output signal.

5. A biological object detecting system according to claim 3, wherein the photodetector means comprises:
- plural photodetectors having respective light receiving faces disposed in adjacent relationship at the predetermined location and producing respective, independent electrical output signals corresponding to the respective levels of light incident thereon, said imaging optical means forming the image of the irradiated portion of the sample on the light receiving surfaces of the plural photodetectors; and
- means for comparing the output signals of the plural photodetectors with a predetermined reference level and thereby producing the detection output signal.

6. A biological object detecting system comprising:
- means for presenting the surface of a sample for optical scanning and detection as a biological sample;
- means for producing a linearly polarized and condensed irradiation light beam and for directing same to the surface of a sample at said presenting means, thereby to irradiate the surface of the sample with a light beam spot;
- condensing and polarizing optical means for receiving and condensing light reflected and scattered by the irradiated surface of the sample and thereby producing a received and condensed light beam, and for extracting from the received and condensed light beam a component, polarized light beam having a predetermined direction of polarization; and
- photodetector means for detecting the intensity of the component, polarized light beam and producing a detection output signal indicating the detected light intensity of the component, polarized light beam and corresponding indicating whether the sample is a biological object or is not a biological object and instead a replica.

7. A biological detecting system according to claim 6, wherein the condensing and polarizing optical means comprises:
- means for dividing the condensed light beam into first and second light beams, each maintaining the polarization state of the received and condensed light beam;
- means for extracting from the first and second light beams, respective, first and second component, polarized light beams having corresponding, mutually orthogonal directions of polarization;
- photodetector means for detecting the respective intensities of the first and second component, polarized light beams and producing corresponding first and second, detected intensity outputs;
- means for calculating the ratio of the detected intensity outputs and producing a corresponding, intensity ratio output; and
- means for comparing the intensity ratio output with a predetermined value for thereby indicating whether the sample is a biological objector is not a biological object and instead a replica.

8. A biological detecting system according to claim 7, wherein the photodetector means comprises first and second photodetectors for respectively detecting the intensities of the first and second component, polarized light beams.

9. A fingerprint detecting and collating system comprising:
- means for presenting a fingerprint surface portion of a sample finger for optical scanning and detection of the sample finger as a genuine biological finger and not a replica thereof, a light source for producing a light beam, condensing optical means for condensing the light beam from the light source and irradiating the surface of a sample presented for detection with a light beam spot, imaging optical means for condensing light reflected and scattered by the irradiated portion of the sample and forming an image of the irradiated portion at a predetermined location, and photodetector means disposed at the predetermined location for detecting the size of the image of the irradiated portion and, correspondingly, for producing a detection output signal indicating whether the sample is a biological object or a replica; and
- fingerprint collating means, operable in response to the detection output signal indicating the sample to be a biological finger and thus nota replica, means for storing an image of the fingerprint portion of a biological finger with associated identification data, and means for producing and comparing an image of the fingerprint portion of the detected biological finger with the stored fingerprint image and thereby collating same with the stored identification data.

10. A fingerprint image processing system comprising:
- means for presenting the fingerprint surface of a finger sample for optical scanning and detection of the finger sample as a genuine biological finger or as a replica thereof, and for identification of the fingerprint of a detected biological finger;
- a light source producing a light beam;
- a single grating lens for receiving the light beam and producing a first, transmitted light beam and a second, diffracted light beam;
- optical detection means for irradiating the fingerprint surface of a finger sample, as presented, with one of said first and second light beams formed as a light beam spot, for forming an image of the fingerprint surface as irradiated with the light beam spot, and for detecting, from the image of the light beam spot, whether or not the fingerprint surface corresponds to that of a genuine biological finger; and
- identification means responsive to the detection of a genuine biological finger by the detection means for illuminating substantially the complete fingerprint surface of the thus detected genuine biological finger with the other of said first and second light beams, for producing am image of the illuminated fingerprint surface in accordance with the scattered and reflected light produced by illumination thereof, and for determining from the image the identity of the fingerprint, as presented.

11. A fingerprint image processing system according to claim 10, wherein said identifying means utilizes the transmitted light beam produced by the grating lens for completely illuminating the fingerprint surface of the finger sample, and said detecting means utilizes the diffracted light beam produced by the grating lens for irradiating the fingerprint surface with the light beam spot.

12. A fingerprint image processing system according to claim 10, wherein:

said detecting means utilizes the transmitted light beam produced by the grating lens for irradiating the fingerprint surface with the light beam spot and said identifying means utilizes the diffracted light beam produced by the grating lens for completely illuminating the fingerprint surface.

13. A fingerprint image processing system according to claim 10, wherein the presenting means comprises a transparent light guiding body on which the fingerprint surface of the finger sample is placed for optical scanning and detection.

14. A fingerprint image processing system according to claim 13, wherein said grating lens is formed on the transparent light guiding body.

15. A fingerprint image processing system according to claim 14, wherein said transparent light guiding body has first and second parallel surfaces, the fingerprint surface of the finger sample being received on the first parallel surface, and a slanted, edge surface forming an acute angle with the first parallel surface on which the first and second light beams are incident for transmission through the transparent light guiding body and to the first parallel surface for the illumination and irradiation of the fingerprint surface, as aforesaid.

16. A fingerprint image processing system according to claim 15, wherein said grating lens is formed on the slanted surface.

17. A fingerprint image processing system according to claim 13, wherein the width of the light beam spot is greater than the spacing between the ridges of a fingerprint.

18. A fingerprint image processing system according to claim 17, wherein the width of the light beam spot is greater than 1 mm.

19. A fingerprint image processing system according to claim 18, wherein the width of the light beam spot is defined by the diameter of the light beam spot.

20. A fingerprint image processing system according to claim 17, further comprising optical means for producing a linear beam of light for irradiating the sample with a light beam spot.

21. A fingerprint image processing system according to claim 20, wherein the width of the light beam spot is defined by the width of the linear light beam.

22. A fingerprint image processing system according to claim 20, wherein said optical means for producing a linear beam of light comprises a cylindrical lens.

23. A fingerprint image processing system according to claim 13, further comprising a common photodetector upon which the respective images formed by irradiation of the fingerprint surface by the biological object detection means and by the identification means are incident.

24. A fingerprint image processing system comprising:
means for presenting the fingerprint surface of a finger sample for optical scanning and detection of the finger sample as a genuine biological finger or as a replica thereof, and for identification of the fingerprint of a detected biological finger;
a light beam source;
means for producing a first light beam from the light beam source;
a single grating lens for receiving light from the light beam source and producing a second, diffracted light beam;
biological object detection means for irradiating the fingerprint surface of a sample finger, as presented, with a light beam spot for forming an image of the fingerprint surface as irradiated with the light beam spot, and for detecting, from the image of the light beam spot whether or not the fingerprint surface corresponds to a genuine biological finger; and
identification means responsive to the detection of a genuine biological finger by the detection means for illuminating the fingerprint surface of the thus detected genuine biological finger with the other of said first and second light beams, for producing am image of the illuminated fingerprint surface in accordance with the scattered and reflected light produced by illumination thereof, and for determining, from the image, the identity of the fingerprint.

25. A fingerprint image processing system according to claim 24, wherein said identifying means utilizes the diffracted light beam produced by the grating lens for entirely irradiating the fingerprint surface.

26. A fingerprint image processing system according to clam 24, wherein said detecting means utilizes the diffracted light beam produced by the grating lens for irradiating the fingerprint surface with the light beam spot.

27. A fingerprint image processing system comprising:
means for presenting the fingerprint surface of a finger sample for optical scanning and detection of the finger sample as a genuine biological finger or as a replica thereof, and for identification of the fingerprint of a detected biological finger;
first light source means for producing a condensed light beam for irradiating the fingerprint surface with a light beam spot at a predetermined location;
imaging optical means for forming an image of the portion of the fingerprint surface produced by irradiation thereof by the light beam spot and for forming an image of the fingerprint surface as substantially completely illuminated by the second light beam at the sample predetermined location;
photodetector means disposed at the predetermined location for receiving each of the aforesaid images and producing corresponding first and second image detector outputs;
biological object detector means responsive to the first image detector output for detecting whether or not the fingerprint surface corresponds to that of a genuine biological finger;
identification means responsive to the detection of a genuine biological finger and to the second image detector output for determining the identity of the fingerprint; and
differentiating means for differentiating between the first and second image detector outputs in accordance with the images received thereon being formed respectively by the first and second light beam sources.

28. A fingerprint image processing system according to claim 27, wherein said differentiating means alternately energizes said first and second light beam sources for emitting the respective first and second light beams thereof and correspondingly, alternately enables the detecting means and the identifying means to respond to the respective, first and second image detector outputs.

29. A fingerprint image processing system according to claim 27, wherein said first and second light source means produce first and second light beams of different wavelengths, and said differentiating means differentiates between the first and second image detector outputs in accordance with the respective, different wavelengths of the first and second light beams and correspondingly of the respective images produced thereby.

30. A fingerprint image processing system according to claim 29, wherein said first and second light source means produce the respective first and second light beams and the first and second corresponding images substantially simultaneously.

* * * * *

UNITED STATES PATENT AND TRADEMARK OFFICE
CERTIFICATE OF CORRECTION

PATENT NO. : 5,077,803
DATED : December 31, 1991
INVENTOR(S) : Masayuki KATO et al.

It is certified that error appears in the above-identified patent and that said Letters Patent is hereby corrected as shown below:

* Col. 1, line 35, change "system" to --systems--.

* Col. 3, line 12, after "comprises" delete ",".

Col. 6, line 10, change "direction" to --directly--;
         line 24, change "$L_2$" to --$L_2'$--;
         line 52, change "$L_2$" to --$L_2''$--.

* Col. 8, line 28, change "provides" to --provide--.

Col. 9, line 32, after "light" insert --beam--;
         line 37, after "light" (second occurrence) insert --beam--.

Col. 10, line 7, after "beam" insert --, as--;
         line 17, change "$V_L$" to --$V_{L1}$--;
         line 21, after "finger" insert --,--;
         line 26, after "40" insert --,--;
         line 27, change "is" to --to be--, and change "a" to --the--.

Col. 11, line 33, change "photodetector-receives" to --photodetector receives--.

Col. 12, line 20, after "beam" insert --,--;
         line 27, before "perpendicular" insert --(--;
         line 37, change "Sa" to --Sa'--;
         line 41, change "detached" to --detected--.

Col. 13, line 9, before "range" insert --difference--.

UNITED STATES PATENT AND TRADEMARK OFFICE
CERTIFICATE OF CORRECTION

PATENT NO. : 5,077,803

DATED : December 31, 1991

INVENTOR(S) : Masayuki KATO et al.

It is certified that error appears in the above-identified patent and that said Letters Patent is hereby corrected as shown below:

Col. 14, line 3, change "incidental to" to --incident on--;
line 7, change "comes" to --comprises--;
line 15, change "beams" to --beam--;
line 17, change "beams" to --beam--;
line 64, change "irradiated" to --irradiate--.

Col. 15, line 6, after "light" (first occurrence) delete "beam", and after "light" (second occurrence) insert --beam--;
line 50, after "light" (first occurrence) delete "beam", and after "light" (second occurrence) insert --beam--;
line 56, after "axis" insert --of--.

Col. 16, line 42, change "illuminated" to --illumination--;
line 56, after "minimum" insert --value--;
line 57, after "quantity" insert --,--.

Col. 18, line 29, change "detecting circuit 162" to --detecting circuit 161--.

Col. 22, line 42, after "means" insert --,--.

Col. 23, line 39, change "corresponding" to --correspondingly--;
line 50, change "respective" to --respectively--;
line 62, change "objector" to --object or--.

Col. 24, line 22, change "nota" to --not a--.

Col. 26, line 21, change "clam" to --claim--;

UNITED STATES PATENT AND TRADEMARK OFFICE
CERTIFICATE OF CORRECTION

PATENT NO. : 5,077,803
DATED : December 31, 1991
INVENTOR(S) : Masayuki Kato, et al.

It is certified that error appears in the above-indentified patent and that said Letters Patent is hereby corrected as shown below:

Column 26, line 21, change "clam" to --claim--.

line 40, change "sample" to --same--.

Signed and Sealed this

Nineteenth Day of October, 1993

Attest:

BRUCE LEHMAN

Attesting Officer    *Commissioner of Patents and Trademarks*